US009603368B2

(12) United States Patent
Gage et al.

(10) Patent No.: US 9,603,368 B2
(45) Date of Patent: Mar. 28, 2017

(54) MICROBIAL CARRIERS FOR TARGETED DELIVERY OF AGRICULTURAL PAYLOADS

(71) Applicant: UNIVERSITY OF CONNECTICUT, Farmington, CT (US)

(72) Inventors: Daniel Joseph Gage, Storrs, CT (US); Leslie M. Shor, Coventry, CT (US); Joseph Lee Gage, Storrs, CT (US); Jamie Lynn Micciulla, Staten Island, NY (US); Rebecca L. Rubinstein, Stafford Springs, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 14/428,162

(22) PCT Filed: Sep. 16, 2013

(86) PCT No.: PCT/US2013/059890
§ 371 (c)(1),
(2) Date: Mar. 13, 2015

(87) PCT Pub. No.: WO2014/043604
PCT Pub. Date: Mar. 20, 2014

(65) Prior Publication Data
US 2015/0264938 A1    Sep. 24, 2015

Related U.S. Application Data

(60) Provisional application No. 61/701,839, filed on Sep. 17, 2012.

(51) Int. Cl.
*A01N 63/00* (2006.01)
(52) U.S. Cl.
CPC ................... *A01N 63/00* (2013.01)
(58) Field of Classification Search
None
See application file for complete search history.

(56) References Cited

FOREIGN PATENT DOCUMENTS

| WO | 85/00752 A1 | 2/1985 |
| WO | 88/08699 A1 | 11/1988 |
| WO | 98/44802 A1 | 10/1998 |
| WO | 03/057861 A2 | 7/2003 |

OTHER PUBLICATIONS

Foreman et al.(When a habitat freezes solid: microorganisms overwinter in ice column of costal Antarctic lake, FEMS Microbiology Ecology , 2011, 76(3), 401-12). ABS.*
Qu et al.(Studies on amoebae and cysts associated with isolation of *Spongospora subterranean* f. sp. subterranean in vitro, Plant Pathology, 2001, 50(4), 420-6). ABS.*
Steinert et al.(*Mycobacterium avium* bacilli grow saprozoically in coculture with Acanthamoeba polyphaga and survive within cyst walls, Applied and Environmental Microbiology, 1998, 64(6), 2256-61). ABS.*
Rastogi et al.(Correlation of encystment and division in Schizopyrenus russelli, J. of Protozoology, 1977, 24(2), 294-6). ABS.*
International Preliminary Report on Patentability for PCT/US2013/059890, issued Mar. 17, 2015.
Rubinstein, et al: "Abstract: Protist-facilitated transport of soil bacteria in an artificial soil micromodel (2013 Annual Meeting)", Nov. 4, 2013 (Nov. 4, 2013).
Michael Bonkowski: "Protozoa and plant growth: the microbial loop in soil revisited", New Phytologist, vol. 162, No. 3, Jun. 1, 2004 (Jun. 1, 2004 ), pp. 617-631.
Krome Ketal: "Grazing of protozoa on rhizosphere bacteria alters growth and reproduction of *Arabi do psis thaliana*", Soil Biology and Biochemistry, Pergamon, Oxford, GB, vol. 41, No. 9, Sep. 1, 2009 (Sep. 1, 2009 ), pp. 1866-1873.
Krome Ketal: "Soil bacteria and protozoa affect root branching via effects on the auxin and cytokinin balance in plants", Plant and Soil; An International Journal on Plant-Soil Relationships, Kluwer Academic Publishers, DO, vol. 328, No. 1-2, 2010, pp. 191-201.
Kreuzer K et al: "Grazing of a common species of soil protozoa (*Acanthamoeba castellanii*) affects rhizosphere bacterial community composition and root architecture of rice (*Oryza sativa* L.)", Soil Biology and Biochemistry, Pergamon, Oxford, GB, vol. 38, No. 7, Jul. 1, 2006 (Jul. 1, 2006), pp. 1665-1672.
Bhattacharyya and Jha, "Plant Growth-promoting rhizobacteria (PGPR): emergence in agriculture," World J Microbial Biotechnol (2012) 28:1327-1350.
Cassidy, et al., "Environmental applications of immobilized microbial cells: a review," Journal of Industrial Microbiology Feb. 1996, 16(2):79-101.
Armitage, J.P., T. P. Pitta, et al. (Aug. 1999). "Transformations in Flagellar Structure ofRhodobacter sphaeroides and Possible Relationship to Changes in Swimming Speed." Journal of Bacteriology 181(16): 4825-4833.
Barker, J. and M. Brown (1994). "Trojan horses of the microbial world: protozoa and the survival of bacterial pathogens in the environment." Microbiology 140(6): 1253-1259.
Bichai, F., P. Payment, et al. (2008). "Protection of waterborne pathogens by higher organisms in drinking water: a review." Canadian ioumal of microbiology 54(7): 509-524.
Cardon, Z. G. and D. J. Gage (2006). "Resource Exchange in the Rhizosphere: Molecular Tools and the Microbial Perspective." Annual Review of Ecology, Evolution, and Systematics 37(ArticleType: research-article I Full publication date: 2006 I Copyright (Q 2006 Annual Reviews): 459-488.
Hayat et al., "Soil beneficial bacteria and their role in plant growth promotion: a review," Ann Microbiol (2010) 60:579-598.

(Continued)

*Primary Examiner* — Alton Pryor
(74) *Attorney, Agent, or Firm* — McDonnell Boehnen Hulbert & Berghoff LLP

(57) ABSTRACT

The present invention provides compositions that include an agriculturally suitable carrier and encysted or sporulated protozoa present on or in the agriculturally suitable carrier, for use in improving plant growth.

13 Claims, 15 Drawing Sheets

(56) References Cited

OTHER PUBLICATIONS

Deng, J., A. Dhummakupt, et al. (2013). "Dynamic dosing assay relating real-time respiration responses of *Staphylococcus aureus* biofilms to changing microchemical conditions." Analytical Chemistry 85: 5411-5419.

First, M. R., N.Y. Park, et al. (2012). "Ciliate Ingestion and Digestion: Flow Cytometric Measurements and Regrowth of a Digestion-Resistant Campylobacter jejuni. "Journal ofEukaryotic Microbiology 59(1): 12-19.

Humphris, S. N., A. G. Bengough, et al. (2005). "Root cap influences root colonisation by Pseudomonas fluorescens SBW25 on maize." Ferns Microbiology Ecology 54(1): 123-130.

Korber, D. R., J. R. Lawrence, et al. (1989). "Effect of Laminar-Flow Velocity on the Kinetics of Surface Recolonization by Mot+ and Motpseudomonas-Fluorescens." Microbial Ecology 18(1): 1-19.

Wang, W., M. Shor, et al. (2005). "Mobility of protozoa through narrow channels." Applied and Environmental Microbiology 71(8)(8): 4628-4637.

Wang, W., L. M. Shor, et al. (2008). "Protozoa Migration in Bent Microfluidic Channels." Appl. Envir. Microbiol. 74(6): 1945-1949.

Weller, D. M. (1988). "Biological-Control of Soilborne Plant Pathogens in the Rhizosphere With Bacteria." Annual Review of Phytopathology 26: 379-407.

\* cited by examiner

MICROBIAL CARRIERS FOR TARGETED DELIVERY OF AGRICULTURAL PAYLOADS

RELATED APPLICATIONS

This application is a U.S. national phase of International Application No. PCT/US2013/059890 filed on Sept. 16, 2013, which claims benefit of U.S. Provisional Application No. 61/701,839, filed Sept. 17, 2012, both of which are incorporated by reference herein in their entirety.

BACKGROUND

The rhizosphere is the zone of soil surrounding plant roots that is under the influence of the root. Microbes in the rhizosphere, such as beneficial biocontrol bacteria, provide essential services for plant hosts. The primary weakness of conventional technologies that deliver bacteria to roots is the failure to deliver enough functional bacteria to the critical locations within the rhizosphere. Beneficial bacteria added in seed coatings often fail to survive and proliferate and/or fail to colonize growing roots. Spatial investigations of beneficial bacteria along roots have shown many empty patches and reduced abundance of beneficial bacteria with distance from seed to root tip. Furthermore, even if biocontrol bacteria do attach to an emerging root, seedling roots grow very quickly from the leading edge, such that beneficial bacteria cannot reproduce fast enough and become dilute at the growing root tip. Thus, improved compositions and methods are needed for delivering beneficial bacteria and other agricultural payloads to vulnerable roots in actively-growing plants.

SUMMARY OF THE INVENTION

In a first aspect, the present invention provides compositions, comprising:
(a) an agriculturally suitable carrier; and
(b) enycysted or sporulated protozoa present on or in the agriculturally suitable carrier.

In one embodiment, the agriculturally suitable carrier is selected from the group consisting of seeds, seed coats, granular carriers, liquid slurry carriers, and liquid suspension carriers. In another embodiment, the enycysted or sporulated protozoa are present in a formulation that is coated over the agriculturally suitable delivery vehicle. In a further embodiment, the composition further comprises an agricultural payload; in one such embodiment, the agricultural payload comprises agriculturally beneficial bacteria. In a further such embodiment, the enycysted or sporulated protozoa are present in a formulation that is coated over the agriculturally suitable delivery vehicle, and wherein the agriculturally beneficial bacteria are dispersed within the formulation.

In a second aspect, the invention provides methods for improved plant growth, comprising delivering the composition of any embodiment or combination of embodiments of the compositions of the invention to soil with an existing plant, or to soil where a plant or seed is to be planted.

DETAILED DESCRIPTION OF THE INVENTION

Figure 1A:
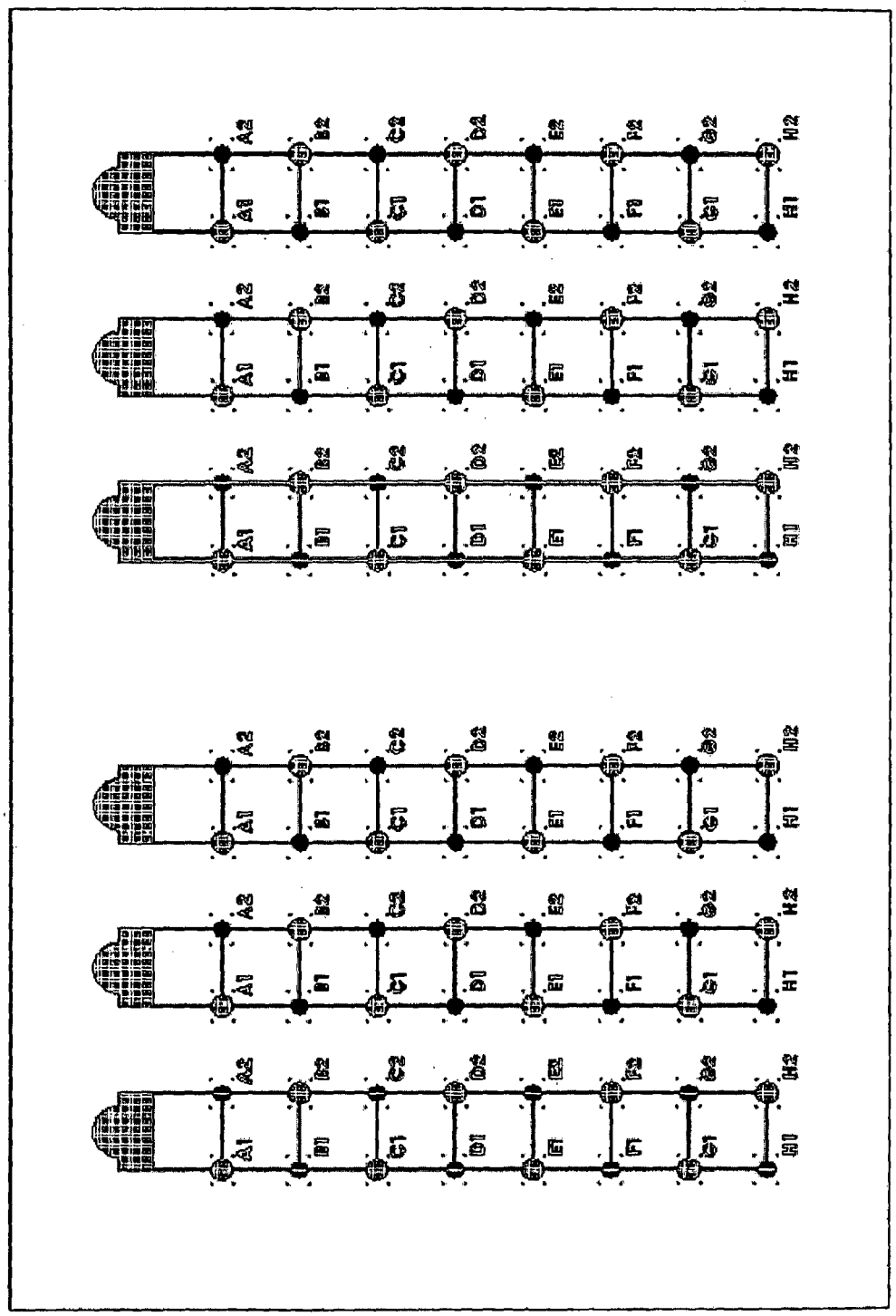
FIG. 1 A. Layout of six identical devices on a single 7.5 cm×5 cm slide. B—Detail of microhabitats and channels with key dimensions.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides compositions, comprising
(a) an agriculturally suitable carrier; and
(b) enycysted or sporulated protozoa present on or in the agriculturally suitable carrier.

The inventors of the present invention have unexpectedly discovered that the compositions of the present invention can be used, for example, to promote significantly improved transport and dispersal of beneficial bacteria and other agricultural payloads to rapidly growing plant roots by active transport via protozoan (also referred to herein as "protist") carriers than would be possible in the absence of the protozoan carriers.

As used herein, the enycysted or sporulated protozoa is present on or in the agriculturally suitable carrier, meaning that the enycysted or sporulated protozoa may be coated directly on the carrier, may be present in a layer that overlays the carrier, may be present within a carrier, or there may be one or more layers interposed between the enycysted or sporulated protozoa and the carrier.

As used herein, an "agriculturally suitable carrier" is any carrier on which the protozoa can be placed on or in to facilitate transport of agricultural payloads to the growing roots of a plant, and which is otherwise suitable for agricultural use. Regardless of the carrier used, the compositions of the invention allow for transport of the agricultural payload to the growing roots, since the protozoa are efficiently mobile in soils and will naturally target the roots. Thus, regardless of the specific agricultural payload or the concentration at which it is used, the compositions of the present invention will provide for a more effective delivery. Any such suitable carrier can be used, including but not limited to seeds, seed coats, granular carriers, liquid slurry carriers, and liquid suspension carriers. The carrier may constitute a majority of the composition (by volume or weight). Any suitable size of carrier can be used as determined most appropriate for a given application. In various non-limiting embodiments, standard sizes of powder-based carriers may vary from 75 μm to 0.25 mm in diameter, or granules and beads may range from 100-200 μm to 3-4 mm in diameter.

In one embodiment, the agriculturally suitable carrier comprises a seed or seed coat ("seed-based carrier"). As will be understood by those of skill in the art, a seed-based carrier composition may comprise a single seed or multiple seeds. In this embodiment, the encysted or sporulated protozoa may be present directly on the seed-based carrier, or may be present in a formulation layered over the seed-based carrier (i.e.: "encapsulated seeds"). In various embodiments, the formulation layered over the seed-based carrier may comprise or consist of granular materials, liquid slurries, biopolymers (such as biopolymer gels), and liquid suspensions. Such formulations may comprise organic materials, inorganic materials, or materials synthesized from specific molecules. Dry carriers can be produced using different kinds of soil materials (peat, coal, clays, inorganic soil), organic materials (composts, soybean meal, wheat bran, sawdust, etc.), or inert materials (e.g., vermiculite, perlite, kaolin, bentonite, silicates). Liquid carriers can be based on broth cultures, mineral or organic oils, or on oil-in-water suspensions. In the case of solid carriers, powder, granules, or beads can be used. Any other materials suitable for encapsulating seeds may also be used with the carriers of the present invention.

Such formulations may further comprise any other materials as deemed suitable for an intended use of the composition, including but not limited to polymers, bulking agents, and any other suitable component. In various non-limiting examples, powders can be used to coat seed-based carriers, or can be suspended in a liquid to form a slurry that is directly applied to the seed-based carrier, using standard techniques in the art.

In another embodiment, the agriculturally suitable carrier comprises a granular carrier, liquid slurry carrier, or liquid suspension carrier ("non-seed based carrier"), and the encysted protozoa are present on or in the carrier. Such carriers may comprise organic materials, inorganic materials, or materials synthesized from specific molecules. Dry carriers can be produced using different kinds of soil materials (peat, coal, clays, inorganic soil), organic materials (composts, soybean meal, wheat bran, sawdust, etc.), or inert materials (e.g., vermiculite, perlite, kaolin, bentonite, silicates). Liquid carriers can be based on broth cultures, mineral or organic oils, or on oil-in-water suspensions. In the case of solid carriers, powder, granules, or beads can be used. In these embodiments, the encysted protozoa may be present directly on the non-seed based carrier, or may be present within the volume of the non-seed based carrier, which may further comprise any other materials as deemed suitable for an intended use of the composition, including but not limited to polymers, bulking agents, and any other suitable component.

The carrier preferably has a sufficient shelf life, and preferably allows an easy dispersion or dissolution in the volume of soil near the root system. A preferred carrier would thus have one or more properties including good moisture absorption capacity, easy to process and free of lump-forming materials, near-sterile or easy to sterilize by autoclaving or by other methods (e.g., gamma-irradiation), and good pH buffering capacity. For carriers that are used for seed coating, good adhesion to seeds is preferable.

Many protozoans respond to adverse environmental conditions by encystment or sporulation. For example, encysting, which involves secretion of a thick wall ('cyst") surrounding the protozoan and effectively entering a resistant dormant state. Such adverse environmental conditions include, but are not limited to, changes in temperature, aquatic acidity, food supply, moisture, and light. Protozoans will typically jettison partially-digested food particles in food vacuoles prior to encystations. When the environment is once again suitable for the protozoan, the cyst wall breaks down, a process known as excystation. Sporulation is another mechanism some protozoa use for responding to adverse environmental conditions. Inducing protozoan encystment or sporulation is well within the level of skill in the art, and the techniques used to do so will depend on the protozoan species to encyst or sporulate. Exemplary means to induce protozoan encystment or sporulation include, but are not limited to, gently drying a liquid culture or by depletion of the food supply.

The encysted or sporulated protozoa are present on or in the agriculturally suitable carrier. The encysted or sporulated protozoa for use in the present invention are those which are motile when not in an encysted or sporulated state. In use the compositions are placed in soil where a plant is growing (non-seed based carriers), or to soil where a seed is to be planted (seed-based carrier) or a plant is to be planted (non-seed-based carriers). After placement of the composition with appropriate encysted or sporulated protozoan in the soil, the protozoa will remain encysted or sporulated until soil conditions are suitable for the protozoan to emerge. Suitable conditions include adequate moisture, appropriate temperature, and proximity of a root tip. Protozoans emerge from cysts as a direct response to proximity to a growing root tip. Once protozoans emerge, they continuously and indiscriminately feed upon bacteria-sized particles in their vicinity. Protozoans are capable of actively transporting these particles a distance equal to the motility rate of the protozoan times the residence time of particles contained within or attached along the exterior surface of the protozoan. As shown in the examples that follow, such active transport of agricultural payloads (such as beneficial bacteria) is much more rapid than would be seen in the absence of active transport via the protozoan carriers.

Any suitable protozoan species that is capable of (a) encystment or sporulation, and (b) motility can be used in the compositions of the present invention. The specific type of protozoan to use in a composition will depend on all variables, including but not limited to the vehicle to be used, the plant to be treated with the composition, the soil type, the agricultural payload to be delivered in conjunction with the protozoa, etc. In various non-limiting embodiments, the protozoan may be of the genus *Acanthamoeba, Dictyostelium, Heteromita, Vahlkampfia, Stachyamoeba, Proleptomonas*, Class COLPODEA, *Thecamonas, Bodo, Neobodo, Dimastigella, Rhynchomonas, Ochromonas, Spumella, Tetrahymena, Euplotes, Blepharisma, Vorticella, Hartmannella, Phalansterium, Colpoda, Cercomonas, Phalansterium*, and combinations thereof. In non-limiting specific examples, the protozoan may be *Colpoda* sp., *Cercomonas* sp., and combinations thereof.

In a further embodiment, the composition further comprises an agricultural payload. As used herein, and "agricultural payload" is any component that can be transported to the growing roots of a plant via the compositions of the invention and which can provide a benefit to the plant. Any such suitable payload can be delivered, including but not limited to beneficial bacteria, and nanoparticles or nanoparticles aggregates, either distributed individually or contained in or on a bacteria-sized carrier, and micro-sized pellets or capsules including liposomes or polymerosomes containing any compound currently used in corporate agriculture. Examples include fertilizers or other plant nutrients (i.e., bioavailable nitrogen or phosphorous), pesticides especially nematicides, fungicides, or bactericides effective against pathogenic bacteria.

In a preferred embodiment, the payload comprises agriculturally beneficial bacteria. As used herein "agriculturally beneficial bacteria" are bacteria that can confer any type of benefit to a growing plant, including but not limited to nitrogen fixation, suppression of plant pathogen activity, production of antibiotics and growth factors, mobilization of nutrients from soil, moderating soil moisture, etc. Any such suitable agriculturally beneficial bacteria can be used in the compositions of the present invention. The specific type of bacteria to use in a composition will depend on all variables, including but not limited to the vehicle to be used, the plant to be treated with the composition, the protozoa used, the soil type, etc. In various non-limiting embodiments, the bacteria may be of the group Rhizobiales, Psedomonadaceae, Bacillaceae, Rhososprillaceae, Psecomonadaceaea, and combinations thereof. In non-limiting specific examples, the bacteria may comprise *Sinorhizobium* species, *Rhizobium* species, *Mesorhizobium* species, *Bradyrhizobium* species, *Bacillus* species, *Pseudomonas fluorescens, Pseudomonas putida, Azospirillum brasilense, Azotobacter vinelandii*, and combinations thereof. Other exemplar bacteria include, but are not limited to *Aeromonas veronii, Agrobacterium* sp., *Alcaligenes piechaudii, Comamonas acidovorans, Enterobacter cloacae, Rhizobium leguminosarum, Paenibacillus polymyxa, Methylobacterium fujisawaense, B. campestris Bacillus circulans* DUC1, *B. firmus* DUC2, *B. globisporus* DUC3, *Alcaligenes* sp. *Bacillus pumilus, Pseudomonas* sp., *Variovorax paradoxus, Enterobacter cloacae, Pseudomonas cepacia*, L. *Enterobacter sakazakii* 8MR5, *Pseudomonas* sp. 4MKS8, *Klebsiella oxytoca* 10MKR7, *L. Pseudomonas* sp., *Bacillus subtilis, Crocus sativus* L, *B. cereus, Salvia miltiorrhiza, Azospirillum* sp., *Azoarcus* sp., *Azotobacter* sp., *Bacillus polymyxa, Burkholderia* sp., *Gluconacetobacter* sp., *Herbaspirillum* sp., *Bacillus amyloliquefaciens, Bacillus pumilus* SE 34, *Streptomyces marcescens* 90-116, *Bacillus licheniformis, Paenibacillus polymyxa* E681, *Enterobacter* sp., *Pseudomonas aeruginosa, Bacillus amyloliquefaciens, Sinorhizobium meliloti*, and combinations thereof (See Bhattacharyya and Jha, World J Microbiol Biotechnol (2012) 28:1327-1350; see also Hayat et al., Ann Microbiol (2010) 60:579-598)

The bacteria can be directly coated on the enycysted or sporulated protozoa (for example, co-locating bacteria immobilized at high concentrations in a formulation, such as a biopolymer gel with encysted protozoans; see, for example, Journal of Industrial Microbiology February 1996, 16(2):79-101); for example, this embodiment facilitates ingestion of bacteria by the protozoa following release from dormancy after placement of the compositions for use in promoting plant growth. Alternatively, the bacteria may be present dispersed within the non-seed carrier and/or formulation as appropriate for a given composition. The composition may comprise any amount of bacteria as suitable for a given purpose. In one non-limiting embodiment where the bacteria are dispersed in a formulation, the compositions would preferably have at least 50,000 bacteria; preferably at least 100,000, 250,000; 500,000, or more bacteria per seed. In another non-limiting embodiment where the bacteria are present on the protozoa, the bacteria can be present at 10 bacteria or more per protozoan; in preferred embodiments at 25, 50, 75, 100, or more bacteria per protozoan.

Any suitable ratio of protozoa to bacteria can be present in the bacteria-containing compositions of the invention. The specific ratio to use in a composition will depend on all variables, including but not limited to the vehicle to be used, the plant to be treated with the composition, the protozoa and bacteria to be used, used, the soil type, soil moisture etc. In one non-limiting embodiment, the protozoa:bacteria in the composition is between about 1:50 to 1:10,000. In various further embodiments, the ratio is between about 1:50 to 1:5000, 1:50 to 1:2500, 1:50 to 1:1000, 1:50 to 1:500, 1:100 to 1:10,000, 1:250 to 1:10,000, 1:500 to 1:10,000, 1:1000 to 1:10,000, 1:100 to 1:5000, 1:100 to 2500, 1:100 to 1:1000, 1:250 to 1:10,000, 1:250 to 1:5000, 1:250 to 1:2500, 1:500 to 1:10,000, 1:500 to 1:5000, and about 1:1000 to 1:10,000.

The composition of any embodiment or combination of embodiments of the invention may further comprise an outer coating, to provide improved structural integrity of the composition, which is particularly advantageous for improving storage life of the compositions of the invention, or for selective breakdown of the coating material once a certain temperature or moisture condition suitable for germination is achieved. Any suitable coating can be used; the specific coating to be used will depend on all specifics of the particular composition on which the outer coat is to be placed. Exemplary coatings include, but are not limited to, loam, starch, tyllose (cellulose derivative) or polyacrylate/polyacrylamide polymers, lime, diatomaceous earth, calcium carbonate, talc, silica, kaolin-clay, zeolite, bentonite, vermiculitem proprietary polymers, and combinations thereof. The coatings may comprise any other suitable components, such as binders. Such binders may include, but are not limited to, starch, polyvinyl alcohol, carboxymethyl cellulose, methyl cellulose, and gelatin. It is well within the level of skill in the art to determine an appropriate outer coating for a particular composition of the invention, based on the teachings of the present application.

In a second aspect, the present invention provides methods for improved plant growth, comprising delivering the composition of any embodiment or combination of embodiments of the invention to soil with an existing plant, or to soil where a plant or seed is to be planted. In a preferred embodiment, the compositions for use in the methods of the invention comprise an agricultural payload, such as beneficial bacteria. The inventors of the present invention have unexpectedly discovered that the compositions of the present invention can be used, for example, to promote significantly improved transport and dispersal of beneficial bacteria and other agricultural payloads to vulnerable root tips of actively growing plants by active transport via protozoan carriers than would be possible in the absence of the protozoan carriers. Details of the compositions for use in the methods of the invention are provided above in the first aspect of the invention.

In embodiments where the carrier is a seed-based carrier, the methods may comprise delivering the composition to soil where the seed is to be planted. In embodiments where the carrier comprises a non-seed based carrier, the methods may comprise administering the composition to soil with an existing seed or plant. Other suitable uses of the compositions in the methods of the invention will be apparent to those of skill in the art based on the teachings herein. In an exemplary embodiment, seeds are coated with enycysted or sporulated protozoa and are co-located with beneficial bacteria in a formulation (such as a biopolymer gel) coated over the seed. The seeds are then planted and, as the seeds germinate and first roots form, the enycysted or sporulated protist senses proximity to a growing root, excysts (or otherwise exits dormancy), and immediately begin seeking prey. Beneficial bacteria may be transported by protozoans either by engulfing/ingesting or by carriage on exterior protist surfaces. As the early plant develops, the protozoa transport the bacteria along the rapidly growing plant roots. As plant growth continues, the released bacteria colonize the rhizosphere zone of soil directly surrounding the plant roots. The majority of bacteria consumed and lysed nevertheless provide nutrients to the minority of bacteria that are transported intact and able to reproduce. The periodic death of a protist filled with food vacuoles containing bacteria at various stages of digestion is also a mechanism for seeding colonies of beneficial bacteria along growing plant roots.

In an alternative exemplary embodiment, a non-seed based carrier composition includes enycysted or sporulated protozoa and are co-located with beneficial bacteria immobilized in a formulation (such as a biopolymer gel) coated over the non-seed based carrier. The compositions are then delivered to a site where a seed is to be planted or has already been planted, as the seeds germinate and first roots form, the protist excysts (or otherwise exits dormancy) and the resulting motile protozoa transport (for example, by engulfing/ingesting) beneficial bacteria in the composition and are thus able to transport them as described above.

As used herein, "improved plant growth" includes any benefit that the plant may derive that improves plant growth or health, including but not limited to faster growth, improved disease resistance, improved drought tolerance, higher yield, etc. The methods of the invention can be used to improve growth of any plant, including but not limited to crop plants, ornamental plants, trees, grasses, etc. Exemplary crop plants for which the methods of the invention can be used, include, but are not limited to fruits, vegetables, and grains including wheat, rice, corn, soybeans, beans, peanuts, potatoes, cassava, cotton, sugar cane, sorghum, tobacco, radishes, lettuce, tomatoes, peppers, alfalfa, etc.

Specifics of the composition, particularly the beneficial bacteria, for a given use will depend on the plant/seed to be treated. Those of skill in the art will be able to determine an appropriate type of beneficial bacteria to be used in conjunction with the methods of the invention as applied to a particular plant type. In various non-limiting examples, compositions comprising the following beneficial bacteria may be used in conjunction with the recited plant:

*Aeromonas veronii* (Rice)
*Agrobacterium* sp. (Lettuce)
*Alcaligenes piechaudii* (Lettuce)
*Azospirillum brasilense* (Wheat)
*Bradyrhizobium* sp. (Radish)
*Comamonas acidovorans* (Lettuce)
*Enterobacter cloacae* (Rice)
*Rhizobium leguminosarum* (Radish)
*Cytokinin Paenibacillus polymyxa* (Wheat)
*Pseudomonas fluorescens* (Soybean)
*Rhizobium leguminosarum* (Rape & lettuce)
*Bacillus* sp. (Alder)
*Methylobacterium fujisawaense* (Canola)
*Bacillus circulans* DUC1, *B. firmus* DUC2, or *B. globisporus*
DUC3 (*Brassica campestris*)
*Alcaligenes* sp. *Bacillus pumilus, Pseudomonas* sp., or *Variovorax paradoxus* (*Brassica napus*)
*Enterobacter cloacae* (*Brassica napus*)
*Azospirillum brasilense* Cdl843 (*Dianthus caryophyllus*)
*Pseudomonas cepacia* (Soybean)
*L. Rhizobium leguminosarum* bv. *viciae* 128C53 K (*Pisum sativum*)
*Pseudomonas* sp., or *Bradyrhizobium* sp. (Mung bean)
*Pseudomonas putida* (*V. radiata*)
*L. Enterobacter sakazakii* 8MR5, *Pseudomonas* sp. 4MKS8, or *Klebsiella oxytoca* 10MKR7 (Corn)
*L. Pseudomonas* sp. (Corn)
*Pseudomonas fluorescens* (*Catharanthus roseus*)
*P. putida* and *P. fluorescens* (*Hyoscyamus niger*)
*Bacillus subtilis* (*Crocus sativus*)
*B. cereus*, or *Salvia miltiorrhiza* (Bunge)
*Azospirillum* sp. (Maize, Rice, Wheat)
*Azoarcus* sp. (Kallar grass, Sorghum)
*Azotobacter* sp. (Maize, Wheat)
*Bacillus polymyxa* (Wheat)
*Burkholderia* sp. (Rice)
*Gluconacetobacter* sp. (Sorghum, Sugarcane)
*Herbaspirillum* sp. (Rice, Sorghum)
*Bacillus amyloliquefaciens* (Tomato)
*Pseudomonas fluorescens* (Tobacco)
*Bacillus pumilus* SE 34 (Tobacco)
*Pseudomonas* sp. (Groundnut)
*Streptomyces marcescens* 90-116 (Tobacco)
*Bacillus* sp. (Cucumber)
*Bacillus licheniformis* (Pepper)
*Bacillus cereus* MJ-1 (Red pepper)
*Pseudomonas* sp. (White clover)
*Paenibacillus polymyxa* E681 (Sesame)
*Enterobacter* sp. (Chickpea)
*Azospirillum brasilense* (*Prunus cerasifera* L.)
*Pseudomonas aeruginosa* (Mung bean)
*Bacillus subtilis* G803 (Pepper)
*Bacillus amyloliquefaciens* (Bell pepper)

In a third aspect, the present invention provides methods for improved plant growth, comprising delivering protozoa and beneficial bacteria to soil with an existing plant, or to soil where a plant or seed is to be planted. In this aspect, the protozoa and bacteria are not required to be in a composition of the invention, and can be delivered to the soil by any means, including but not limited to those disclosed above. In one embodiment, the protozoa are encysted or sporulated. All embodiments of the methods, beneficial bacteria, protozoa, plants to be treated, formulations, etc. as disclosed above can be used in this third aspect as well. The inventors of the present invention have unexpectedly discovered that the methods of this aspect of the present invention can be used, for example, to promote significantly improved transport and dispersal of beneficial bacteria and other agricultural payloads to vulnerable root tips of actively growing plants by active transport via protozoan carriers than would be possible in the absence of the protozoan carriers.

EXAMPLE 1

Protist-Facilitated Bacterial Transport in Synthetic Microhabitats

Abstract:

Soil is comprised of a complex jumble of micro-structured mineral grains, soil aggregates, organic material, and distributed water and air phases. Near plant roots, a diverse and abundant microbial community is supported by carbon-rich exudates. In return, beneficial bacteria provide important services for plants. Protists are also an important part of this rhizosphere community. Along with selective grazing on pathogens, and mobilization of limiting nutrients, protists may provide another essential service to the rhizosphere ecosystem: transportation. As experts in rapidly traversing unsaturated soil networks, protists may serve as a distribution mechanism for bacteria in the rhizosphere. Here we provide the first direct evidence for protist-facilitated transport of soil bacteria. We employ water-filled microfluidic networks as synthetic microhabitats to directly observe the dynamics of bacterial distribution in micro-scale channels. Soil protists Colpoda sp. and Cercomonas sp. were initially allowed to disperse in microhabitats, and then fluorescently-labeled Pseudomonas fluorescens and Sinorhizobium meliloti were introduced at one end. We found that, despite predation pressure, the abundance of bacteria far from the introduction point increased more rapidly in the protist treatments than in protist-free controls. Also, while the total abundance of bacteria was reduced by protistan grazing, the distribution of bacteria was more even across all positions and times when protists were present. This research suggests an important function for protists in soils may be spatially distributing microbes of all kinds in the dynamic and discontinuous rhizosphere habitat.

Introduction

Soil bacteria within the rhizosphere benefit plants in several different ways. Beneficial biocontrol bacteria coat roots to prevent colonization by pathogens or suppress pathogens by secretion of iron-sequestering siderophores, and by producing antibiotics (Weller 1988). Beneficial bacteria also fix nitrogen, extract nutrients from soil organic matter, and secrete hydrophilic polymers that help plants in moderating soil moisture.

Beneficial bacteria can greatly improve overall plant health and increase crop yield. However, surveys of bacterial abundance show marked declines in bacterial abundance with distance along growing roots. Spatial investigations of biocontrol bacteria on roots commonly shows many empty patches, and populations that decline linearly with distance from seed to tip (Humphris, Bengough et al. 2005). Roots grow so quickly that bacteria cannot reproduce fast enough to avoid being diluted with length. This leaves the tips, where the maximum exudates concentrations are found, vacant and vulnerable.

As protists graze, some bacteria may attach to exterior surfaces of protists, while others may wedge into the protistan oral cavity. Studies have shown that viable bacteria are egested from the soil protist Colpoda (First, Park et al. 2012). Additional studies have shown that some bacteria can survive ingestion by protists and remain viable when released either by lysis of the host cell or when expelled in vacuoles (Barker and Brown 1994; Bichai, Payment et al. 2008). Although certainly many bacteria exposed to predation are consumed and destroyed, we hypothesize that motile protists can benefit rhizosphere systems through facilitating the spatial distribution of beneficial bacteria.

Experimental Section

Figure 1B:
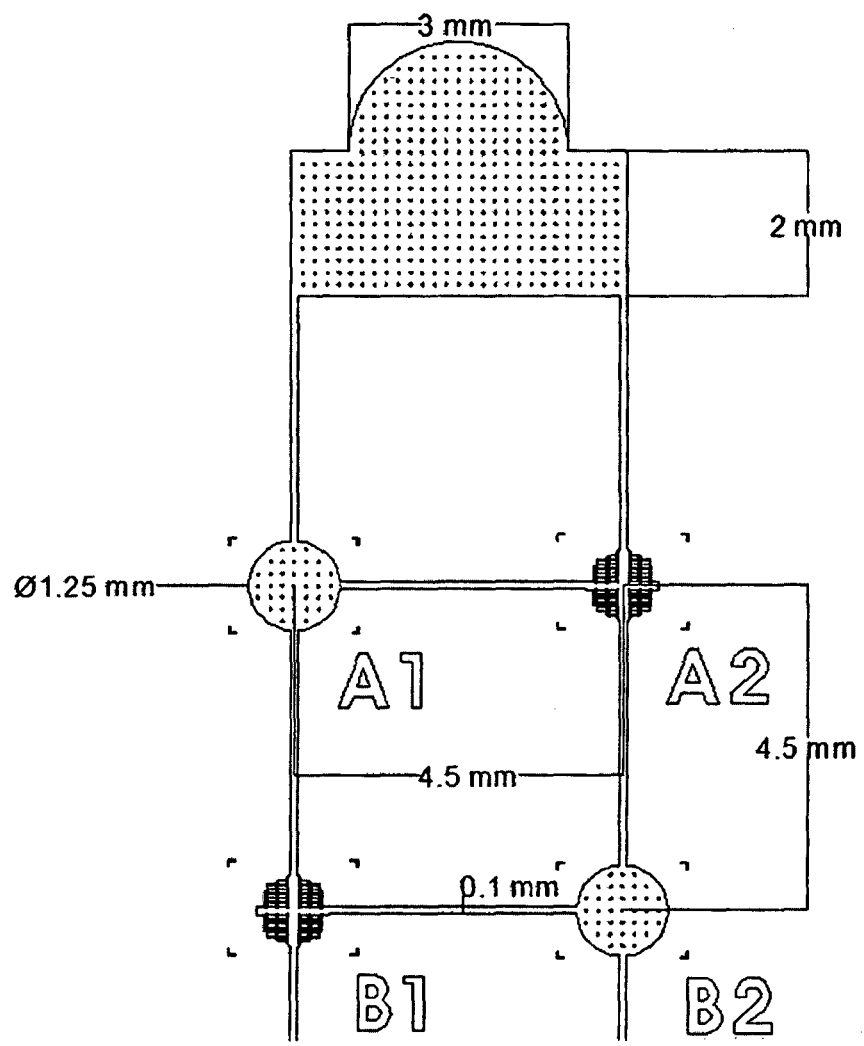

Device Concept. The microfluidic devices used for these experiments were designed to emulate physical features of soil (FIG. 1). Microchannels connecting the entry chamber to the microhabitats are 3.5 mm long, 100 µm wide, and 46 µm high. The microhabitats are either open circular galleries containing only posts or compact networks of 15 µm wide channels, similar to a soil aggregate. The microhabitat types were alternated to emulate the heterogeneous nature of soil, as well as to reduce the effects of clogging. For each trial, six identical devices were arrayed on a single 5×7.5 cm glass microscope slide.

Device Fabrication. A microfluidic master containing six identical microfluidic devices as described above was fabricated using standard methods in photolilthography as described elsewhere Deng et al. (Deng, Dhummakupt et al. 2013) with some slight modifications. Briefly, a 4 inch silicon wafer was spin-coated with SU-8 2025 photoresist to a height of 46±2 µm. The photoresist was patterned by exposure to UV light at 38 mW/cm$^2$ for 4.4 seconds through a mylar emulsion mask (Micro Lithography Services Limited, Chelmsford, Essex, UK). Identical devices were then cast from the developed master using polydimethylsiloxane (PDMS, Sylgard™ 184, Dow Corning, Midland, Mich.).

Biological Cultures and Media. The protists used in this study were Colpoda sp., soil ciliates that form cysts under unfavorable conditions. When active, Colpoda sp. are approximately 30 µm long and 25 µm wide, and when encysted they are spherical with a 30 µm diameter. Non-fluorescent Escherichia coli (strain DH5α) was used to excyst Colpoda prior to the start of each transport experiment. Pseudomonas fluorescens (strain Pf0-1) is a common biocontrol strain, which forms symbiotic relationships with the roots of plants that enhance plant health and improve crop yield. Fluorescently tagged P. fluorescens was used to track protist-facilitated bacterial mobilization by epifluorescence microscopy.

Colpoda were cultured in sterile 1× Page's Saline (Table 1), initially prepared as two separate 10× stock solutions and then combined and diluted as needed. One solution contained the first four ingredients; the second contained only calcium chloride. Escherichia coil (DH5α) and P. fluorescens were cultured in sterile TY media (Table 2). In both cases, media were autoclaved after preparation and at regular intervals thereafter.

TABLE 1

Page's Saline Recipe (10x solutions in 1 L deionized water)

| Chemical name | Mass (g) | Source |
|---|---|---|
| Sodium chloride | 1.2 | Fisher Scientific, Pittsburgh, PA |
| Magnesium sulfate heptahydrate | 0.04 | Fisher Scientific, Pittsburgh, PA |
| Disodium phosphate | 1.42 | Fisher Scientific, Pittsburgh, PA |
| Monopotassium phosphate | 1.36 | Fisher Scientific, Pittsburgh, PA |
| Calcium chloride (anhydrous) | 0.04 | Fisher Scientific, Pittsburgh, PA |

TABLE 2

TY Media Recipe (1 L in deionized water)

| Chemical name | Mass (g) | Source |
| --- | --- | --- |
| Tryptone | 6 | Sigma-Aldrich Corp. St. Louis, MO |
| Yeast Extract | 3 | Fisher Scientific, Pittsburgh, PA |
| Calcium chloride (anhydrous) | 0.38 | Fisher Scientific, Pittsburgh, PA |

Protist—Facilitated Transport Experiments. Replicates were performed in individual PDMS castings created from the photolithography master. Each casting was fabricated into a microfluidic device by first punching a source well at the entry position (FIG. 1) using a 3 mm biopsy punch (Miltex, Inc., York, Pa.). Then, castings were cleaned using isopropanol and masking tape, activated by oxygen plasma and irreversibly bonded to a methanol-cleaned 5 cm×7.5 cm glass slide as described elsewhere (Deng, Dhummakupt et al. 2013).

At the start of each experiment, Colpoda sp. cysts were combined with E. coli in 200 μL of Page's saline and samples were left at room temperature for four hours to allow protists to excyst. Colpoda were then loaded into each microhabitat and allowed to completely distribute for 1 hr. Then, immediately before starting the experiment, stationary-phase triple-washed P. fluorescens were added to source well. Here, 10 μL of liquid was withdrawn from each source well and immediately replaced with 10 μL of P. fluorescens at an $OD_{595}$ of 0.1. Finally, the distribution of the newly-added fluorescent bacteria was tracked in space and time using a fully automated inverted microscope (Zeiss AXIO™-observer Z1 with an AxioCam MRmRev.3 camera, Carl Zeiss Inc., Germany). A time lapse, multi-position experiment was set up on the microscope using Axiovision™ 4.8 software.

Brightfield and fluorescence (470 nm, 62 HE B/G/HR reflector) images were taken using a 5× objective (Zeiss ECPlan-NEOFLUAR™; 5×/0.16 ∞/0.17). The fluorescent images were analyzed using ImageJ™ by applying a threshold to eliminate noise and then computing the number of bright pixels in each frame. The data from the blank device was used to normalize for variations in ambient lighting, and the values for each frame were averaged over the area available to bacteria in that frame to account for different geometries that exist in the device. The fluorescence values were scaled and normalized in order to separate distribution rate from overall changes in the bacterial population.

Results and Discussion

Figure 2:
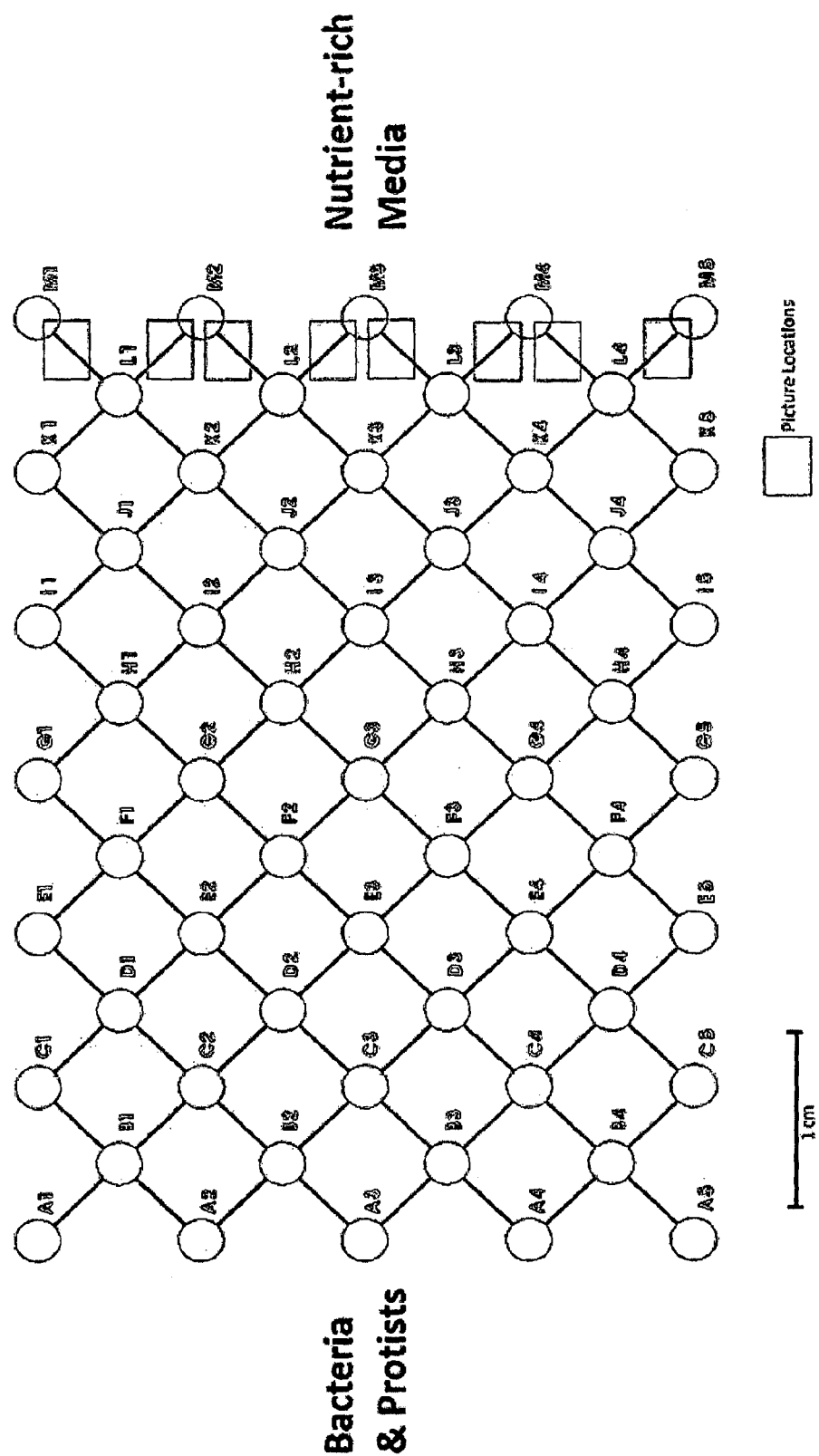
FIG. 2. Device used to obtain qualitative results
Figure 3:
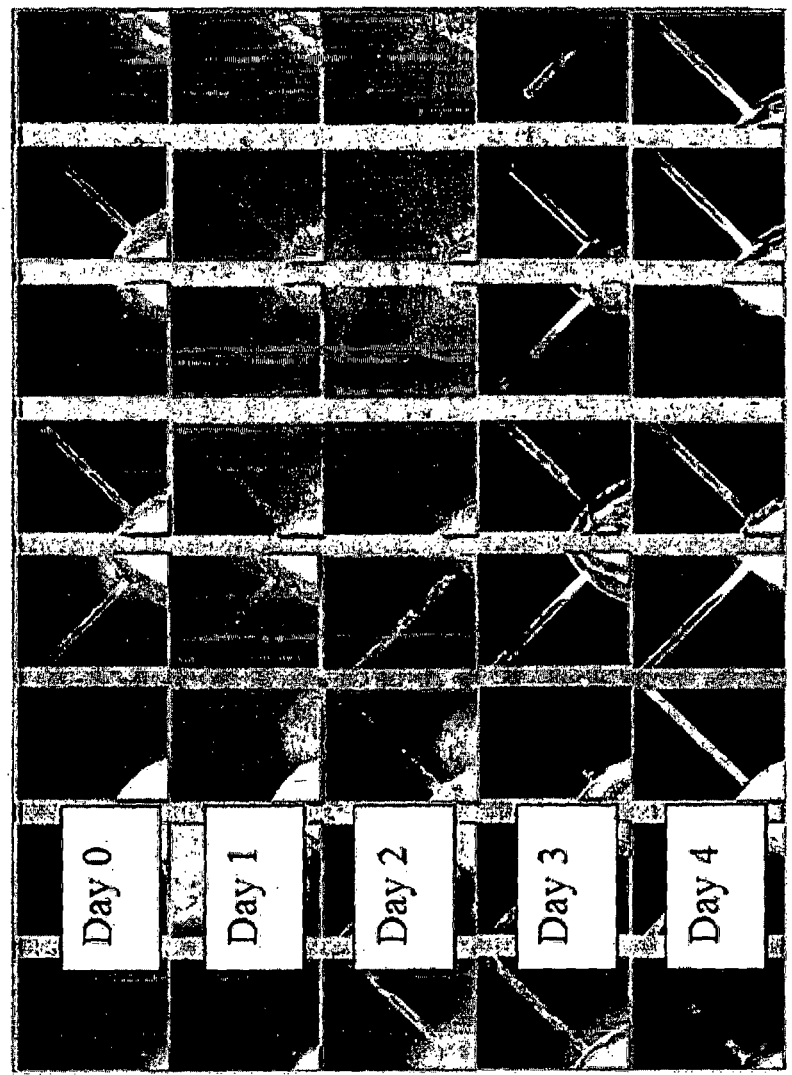
FIG. 3. *P. fluorescens*-Only Treatment, pictures rotated 90 degrees from the orientation shown in FIG. 2.
Figure 4:
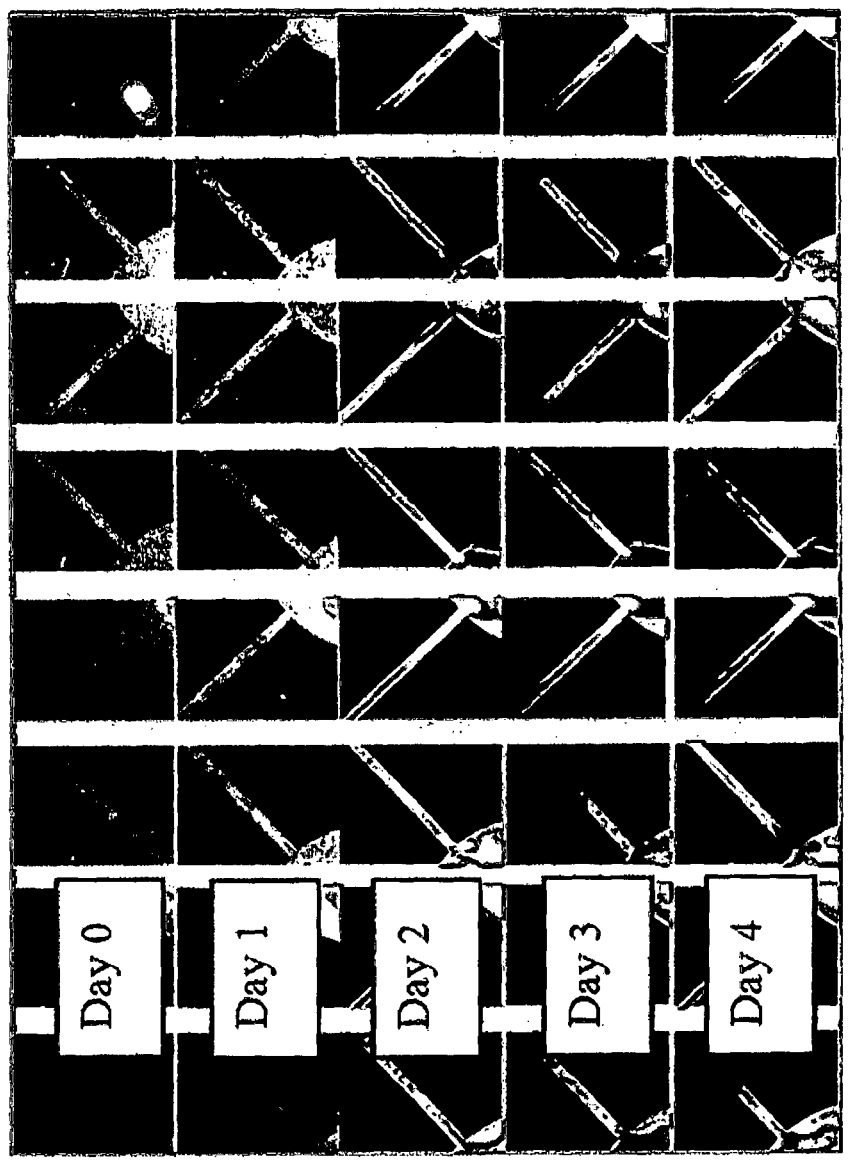
FIG. 4. *P. fluorescens* with *Colpoda* sp., pictures rotated 90 degrees from the orientation shown in FIG. 2.

Preliminary qualitative experiments were performed by loading microbial cultures at one side of a large network of microfluidic channels and using gelled TY media as a chemoattractant at the far end of the device (FIG. 2). Only one treatment at a time was tested with this device, and each device was monitored over the course of 4 days.

It is apparent upon inspection that bacteria in combination with protists began to appear at the far end of the network of channels within 24 hours of loading, while bacteria alone arrived approximately 48 hours after loading.

Figure 5:
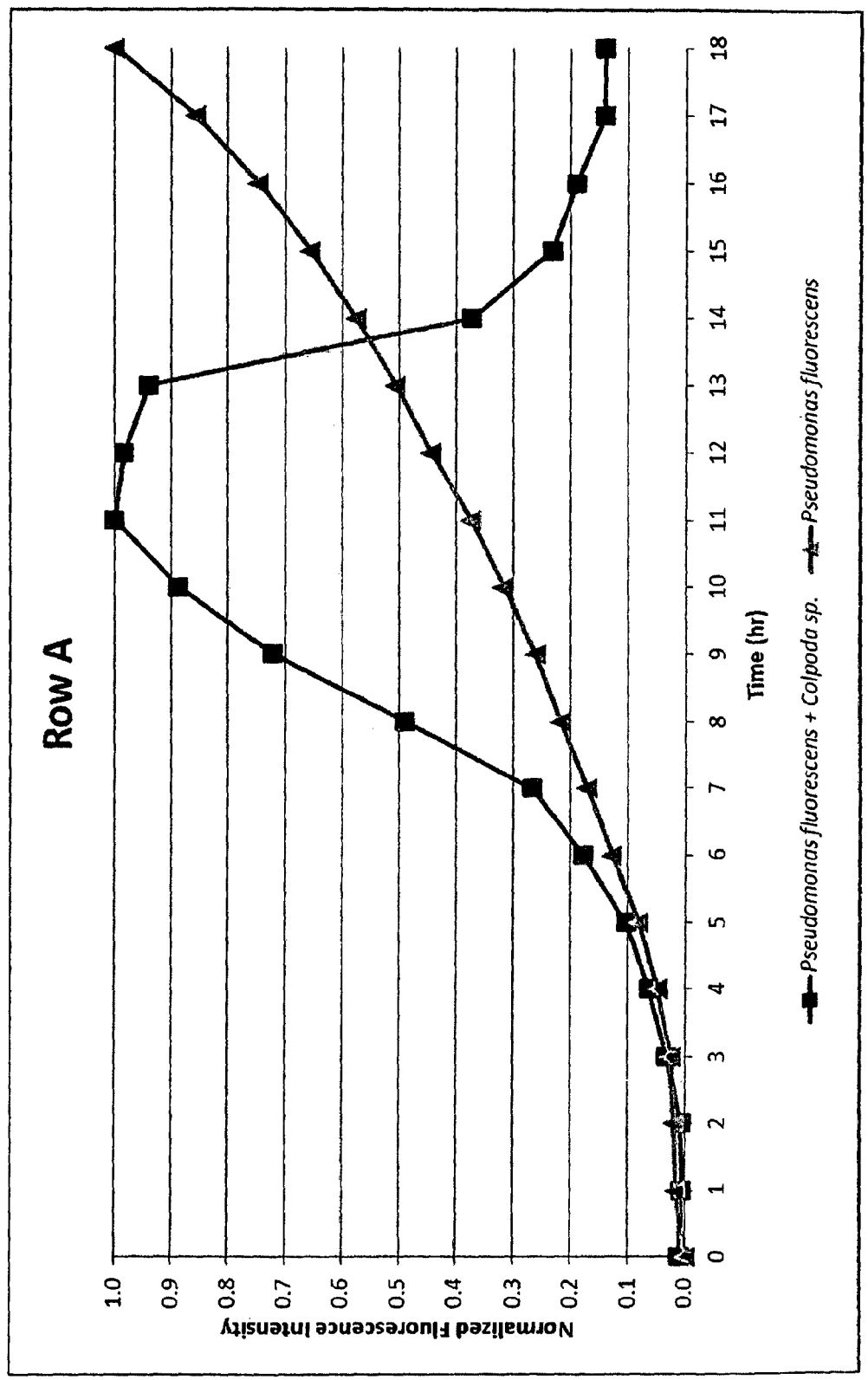
FIG. 5. Area-averaged fluorescence intensity 5.5 mm from microbial inputs, scaled and normalized.
Figure 6:
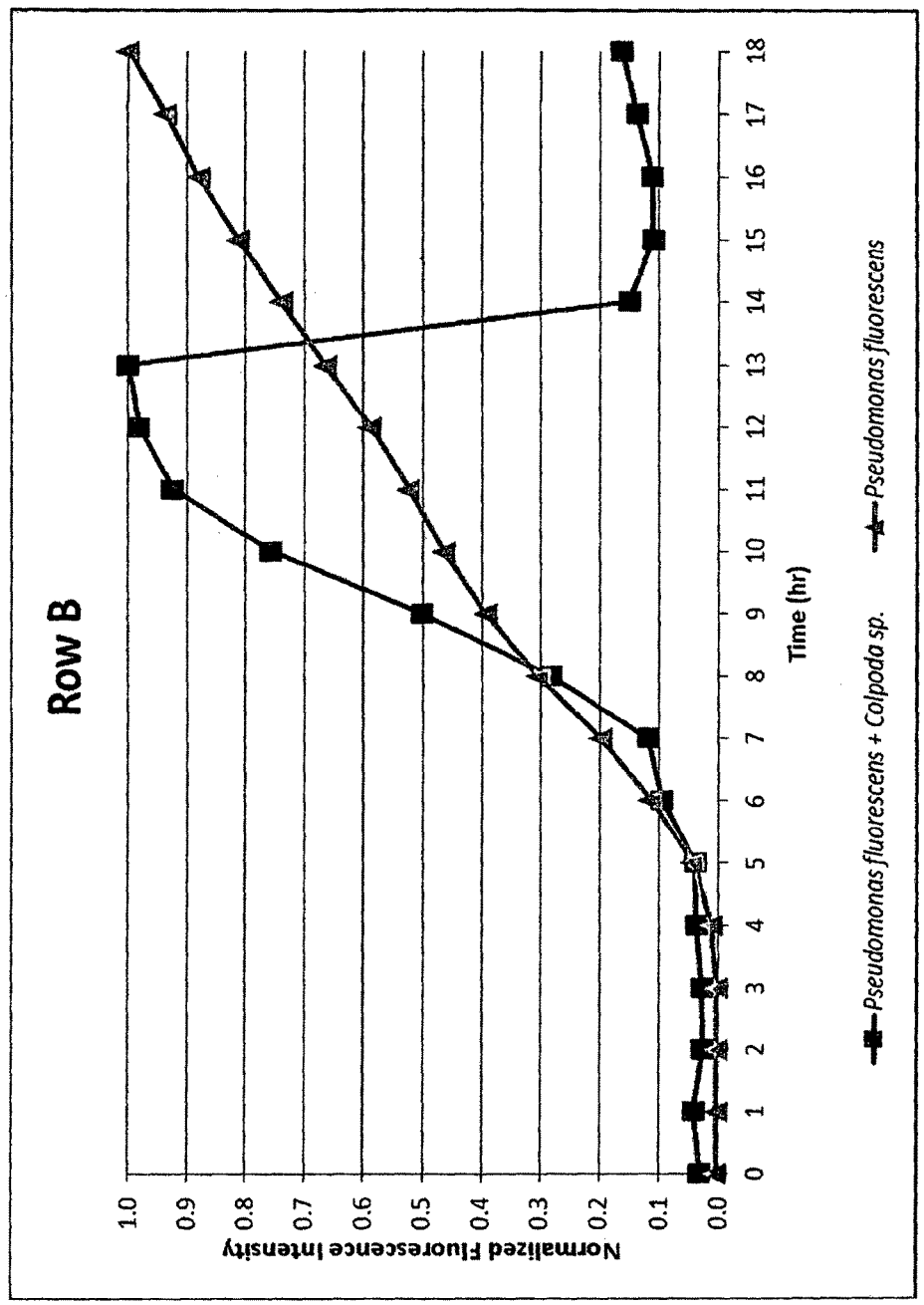
FIG. 6. Area-averaged fluorescence intensity 9 mm from microbial inputs, scaled and normalized.
Figure 7:
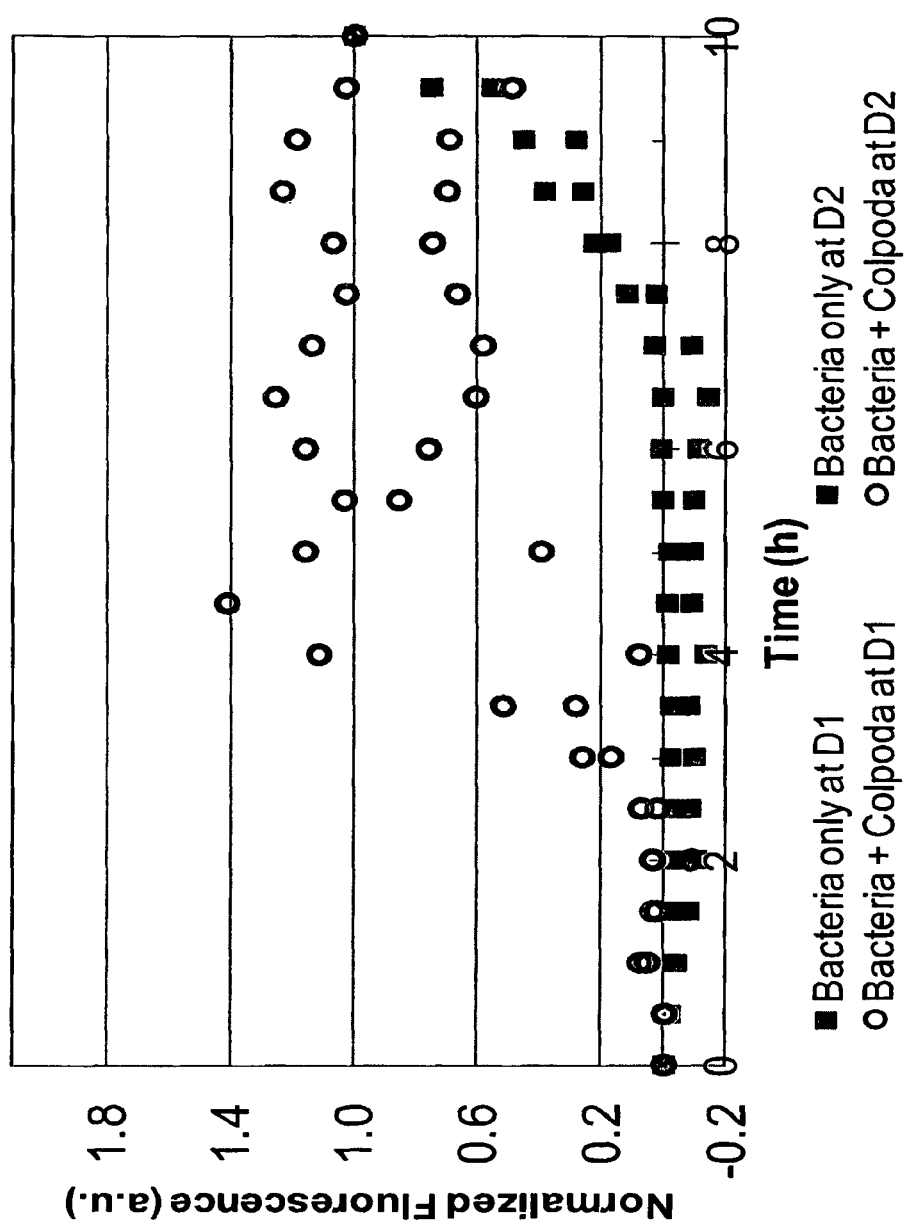
FIG. 7. Protist-facilitated transport: preliminary data showing bacteria arrive on the far side of a microfluidic maze (where there is no flow) in the presence of protists than in the absence of predators.

Following these preliminary trials, shorter and more structured experiments were conducted as described above. Results were judged by comparing bacterial arrival at specific distances along the device for each treatment. For bacteria-only treatments, the population (with normalized fluorescence intensity as an analog for bacterial biomass concentration) consistently showed a gradual increase for the duration of the trial. In treatments containing protists, however, the population peaked hours before the end of the experiment and then declined. The decline is mostly likely due to protist predation on the bacteria, but grazing did not completely eliminate the bacteria in the device. The temporal distribution very clearly shows an early-arrival phenomena in treatments with bacteria+protists (FIGS. 5 and 6).

REFERENCES

Armitage, J. P., T. P. Pitta, et al. (1999). "Transformations in Flagellar Structure of Rhodobacter sphaeroides and Possible Relationship to Changes in Swimming Speed." Journal of Bacteriology 181(16): 4825-4833.

Barker, J. and M. Brown (1994). "Trojan horses of the microbial world: protozoa and the survival of bacterial pathogens in the environment." Microbiology 140(6): 1253-1259.

Bichai, F., P. Payment, et al. (2008). "Protection of waterborne pathogens by higher organisms in drinking water: a review." Canadian journal of microbiology 54(7): 509-524.

Cardon, Z. G. and D. J. Gage (2006). "Resource Exchange in the Rhizosphere: Molecular Tools and the Microbial Perspective." Annual Review of Ecology, Evolution, and Systematics 37(ArticleType: research-article/Full publication date: 2006/Copyright © 2006 Annual Reviews): 459-488.

Deng, J., A. Dhummakupt, et al. (2013). "Dynamic dosing assay relating real-time respiration responses of Staphylococcus aureus biofilms to changing micro-chemical conditions." Analytical chemistry.

Deng, J., A. Dhummakupt, et al. (2013). "Dynamic dosing assay relating real-time respiration responses of Staphylococcus aureus biofilms to changing microchemical conditions." Analytical Chemistry 85: 5411-5419.

First, M. R., N. Y. Park, et al. (2012). "Ciliate Ingestion and Digestion: Flow Cytometric Measurements and Regrowth of a Digestion-Resistant Campylobacter jejuni." Journal of Eukaryotic Microbiology 59(1): 12-19.

Humphris, S. N., A. G. Bengough, et al. (2005). "Root cap influences root colonisation by Pseudomonas fluorescens SBW25 on maize." Fems Microbiology Ecology 54(1): 123-130.

Korber, D. R., J. R. Lawrence, et al. (1989). "EFFECT OF LAMINAR-FLOW VELOCITY ON THE KINETICS OF SURFACE RECOLONIZATION BY MOT+AND MOT−PSEUDOMONAS-FLUORESCENS." Microbial Ecology 18(1): 1-19.

Wang, W., L. M. Shor, et al. (2005). "Mobility of protozoa through narrow channels." Applied and Environmental Microbiology 71(8)(8): 4628-4637.

Wang, W., L. M. Shor, et al. (2008). "Protozoa Migration in Bent Microfluidic Channels." Appl. Envir. Microbiol. 74(6): 1945-1949.

Weller, D. M. (1988). "BIOLOGICAL-CONTROL OF SOILBORNE PLANT-PATHOGENS IN THE RHIZOSPHERE WITH BACTERIA." Annual Review of Phytopathology 26: 379-407.

EXAMPLE 2

Figure 8A:
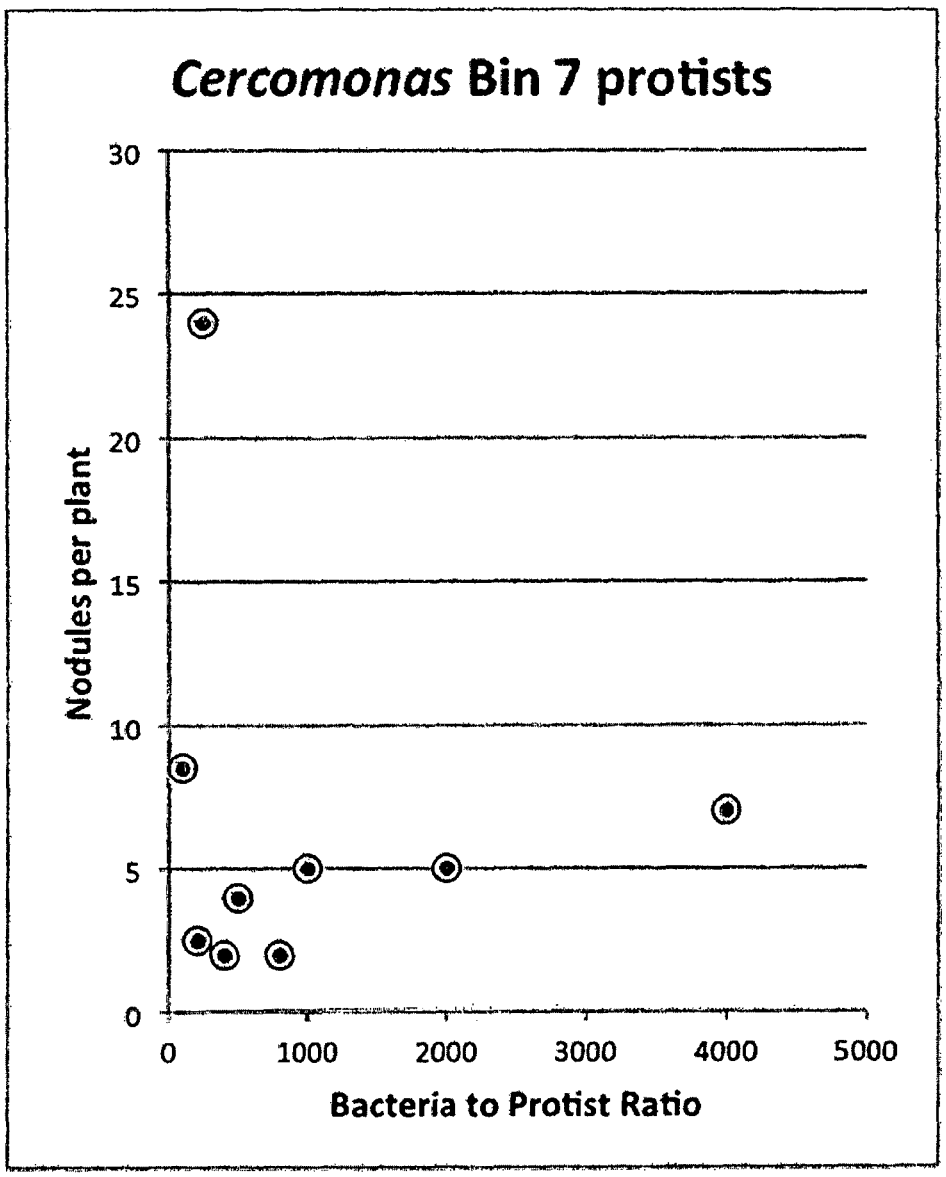
FIG. 8A-B. Effect of the ratio of bacteria: protist ratio on the total number of nodules per bean plant.
Figure 8B:
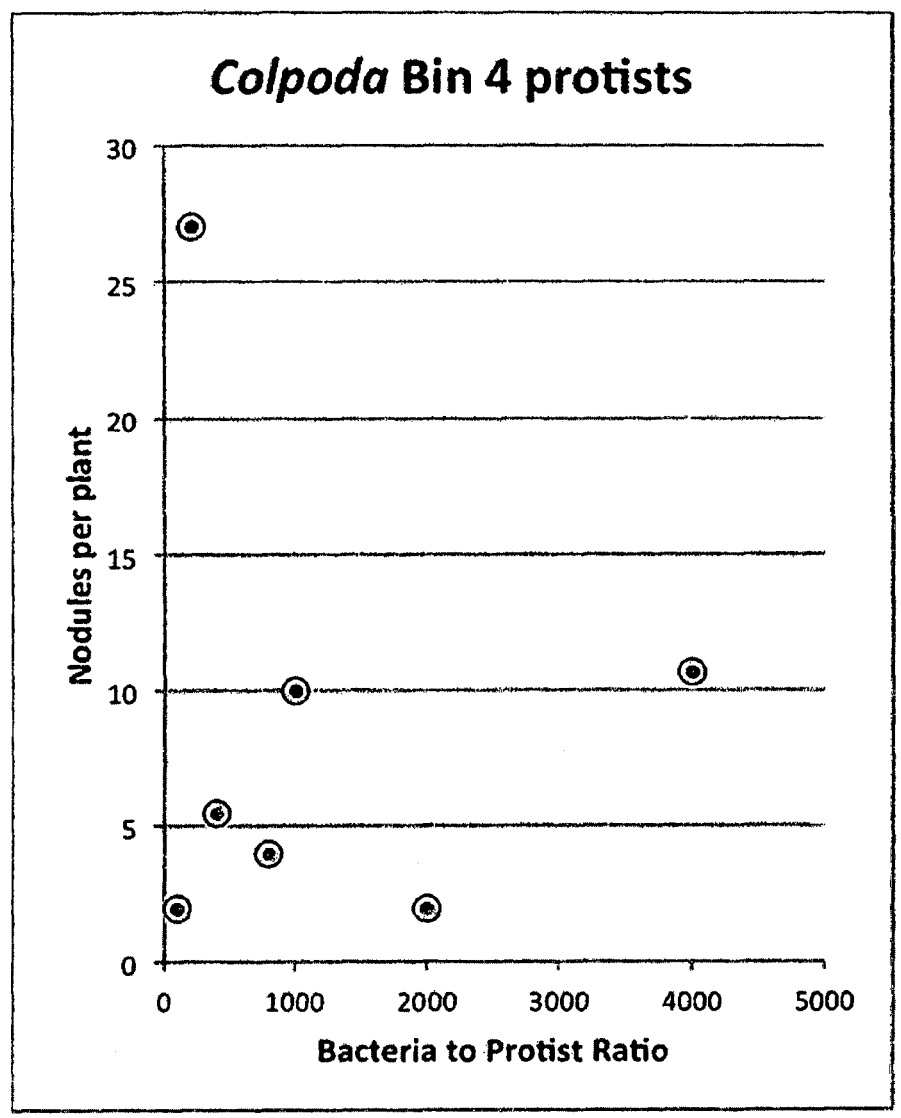

The experiment was intended to determine the optimal inoculation quantities of bacteria and protists for nodule formation and bacterial transport on bean (Phaeseolus vulgaris). The experiment was conducted using the black bean cultivar Zorro™ and a bacterial symbiont of bean, Rhizobium tropici. The seed and bacteria were obtained from Michigan State University. Protists *Colpoda* (Bin4) and *Cercomonas* (Bin7) were used. Seeds were planted using agar plugs treated with pairwise combinations of five quantities of bacteria and five quantities of protist. After ~3.5 weeks, plants were evaluated for total number of nodules along the roots. When total nodules was plotted against the ratio of bacteria to protists, there was a trend across protist types to display a peak around 100-500 bacteria per protist, with decreased nodulation at ratios above and below that range (FIG. 8).

Materials and Methods for Example 2

Agar Plugs:

40 treatments were prepared, following (with a few exceptions) the pairwise combination of 0; 25,000; 100,000; 200,000; and 500,000 bacteria and 0, 100, 250, 500, and 1000 intercepted protists (the number of protist cysts that the root would intersect when it grew through the plug). One type of bacteria (*R. tropici*,) and 2 types of protist (Bin4 *Colpoda* and Bin7 *Cercomonas*) were used.

Treatment matrices are shown below—boxes marked with an "X" were not included.

TABLE 3

| | | Bin4 Protists: | | | | |
|---|---|---|---|---|---|---|
| | | Number of Bacteria Surrounding Seed | | | | |
| | | 0 | 25,000 | 100,000 | 200,000 | 500,000 |
| # of Protists Intercepted by Root | 0 | | | | | |
| | 100 | X | | | | |
| | 250 | X | | | | |
| | 500 | X | | | | |
| | 1,000 | X | X | X | X | X |

TABLE 4

| | | Bin7 Protists: | | | | |
|---|---|---|---|---|---|---|
| | | Number of Bacteria Surrounding Seed | | | | |
| | | 0 | 25,000 | 100,000 | 200,000 | 500,000 |
| # of Protists Intercepted by Root | 0 | | | | | |
| | 100 | X | | | | |
| | 250 | X | | | | |
| | 500 | X | | | | |
| | 1,000 | | | | | |

An additional control treatment consisting of bare, sterilized seeds (not in agar plugs) was planted in 4 pots (2 seeds per pot, to be thinned to 1).

The entire 1000-protist portion of the Bin4 experiment was excluded due to an insufficient stock of encysted protists to enable filling all treatments.

Each treatment was replicated twice, and each replicate was seeded with two plugs, to be thinned down to one.

The number of intercepted protists was calculated based on the diameter of the plate wells that the plugs were poured in (15 mm) and the diameter of an average germinating bean root (2 mm), assuming the root grows in a straight line down perpendicular to the bottom of the plug—the shortest distance that can be covered as long as the root goes through the entire protist layer and does not exit the plug on either side. This provides a conservative estimate of the number of protists intercepted by the root. Plugs were constructed with a number of cysts in the protist layer of the plug that would result in the desired number being intercepted according the specifications above.

Agar plugs were constructed as follows:

Cyst suspension (amount dependent on protist quantity for each treatment) and enough additional Page's saline to bring the total volume to 535 uL were placed in the bottom of each well (e.g., 100 uL cyst suspension and 435 uL Page's).

500 uL of Page's saline with 2% agar (still liquid, no longer hot to the touch) was added to the cyst suspension and mixed well with the pipette.

The mixture was allowed to harden, then a single bean seed was placed in each well on top of the cyst/agar layer.

750 uL of Page's saline with 2% agar (still liquid, no longer hot to the touch) was added on top of the bean and allowed to harden.

The bean seed was disturbed slightly using a sterile wooden applicator so that the seed disconnected from the agar surrounding it (done to ensure that the bacteria injected in the next step had access to the complete surface of the seed).

4.1 uL of bacterial suspension (diluted to achieve the desired number of bacteria in that quantity) was injected with a pipette into the gap between the seed and the agar.

Extra care was taken during plug preparation to keep treatments from cross-contamination. Separate plates were used for each protist type and quantity (i.e., each horizontal row in the matrices above had its own plate), and all controls were given their own plates as well. Page's with 2% agar was dispensed into separate bottles for Bin4, Bin7, and Control treatments to prevent protist cross-contamination. Bacteria were added in the last step to prevent contamination, and Control plates were kept unopened while it was being applied to the other plates.

Planting:

Pots (3 in square×8 in tall) were filled previously with a mixture of 1:1:4 loam:sand:peat, with 1 tablespoons lime added per 2 gallons of mix. They were initially watered 1× or 2× daily to saturate the soil mixture, but due to the hydrophobicity of dry peat had not fully saturated by the day before planting. The racks of pots were placed in large autoclave bins filled almost to the top with water and allowed to draw water from the bottom of the pots, thereby fully saturating the soil. Before planting, pot arrangement was randomized to counteract any gradients in soil mixture composition from filling. 1 or 2 plugs were put in each pot, to be thinned to one plant after germination.

Plugs were removed from the plates with a 25 mL pipette with the tip cut off, used in a manner similar to a cork borer. The cut end of the pipette was pushed into the plug, the other end capped with a finger to create suction, and the plug was removed from the plate and blown out of the pipette into the soil mixture. Great care was taken to avoid cross-contamination, as with plug preparation. A new pipette was used to remove plugs from each different treatment. Researchers did not touch the plugs.

Narrow-stemmed funnels with the stems shortened to ~2 cm long were lined with a cone of filter paper 4 layers thick. Funnel stems were pushed into the soil and water applied by pouring into the filter paper cones. This caused the water to flow slowly out of the funnel, decreasing chances of bulk flow carrying protists and/or bacteria down through the soil. Funnels were autoclaved before being pushed into the soil, so as to prevent contamination.

Roots were washed and nodules counted. One pot at a time, the plants and soil were removed in one piece, then submerged and agitated in water to remove excess soil. The shoot was removed above the cotyledon and put into a manila envelope for drying. The root was subsequently washed further with an overhead sink sprayer to remove remaining soil. It was then measured for total length (starting from seed) and the number of nodules in each 5 cm section of root was counted and recorded (again, starting from seed and moving downward). Roots were discarded after measurement and nodule count. Manila envelopes were put in a hybridization oven set at 70° C. for 3 days, then moved to a desiccator to cool down. Dry shoots were removed from their envelopes and measured on a scale accurate to 0.1 mg. Weight was recorded and shoots were discarded.

EXAMPLE 3

Figure 9A:
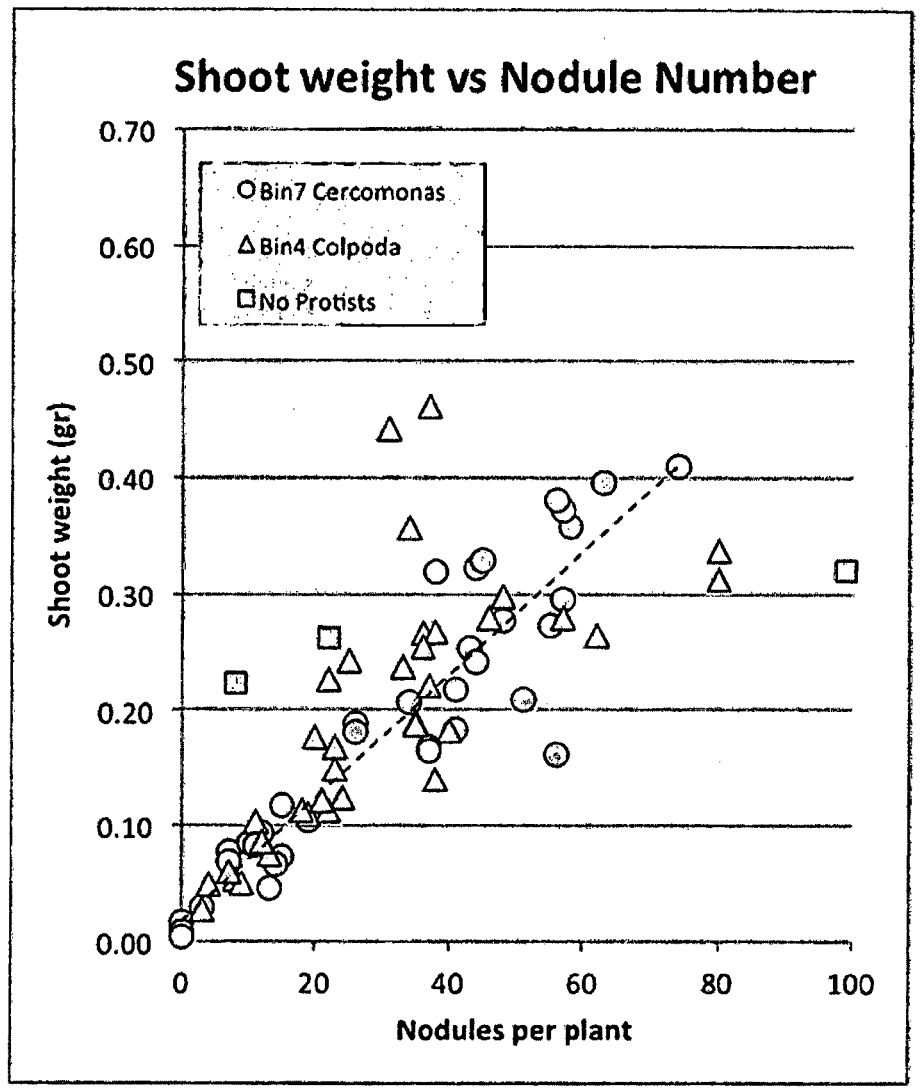
FIG. 9. (A) Total nodules plotted against bean shoot dry weight, colored by protist type. The linear relationship may indicate that plants were nitrogen limited except for what was provided by nodules. (B-C). Effect of the ratio of bacteria: protist ratio on the total number of nodules per bean plant.
Figure 9B:
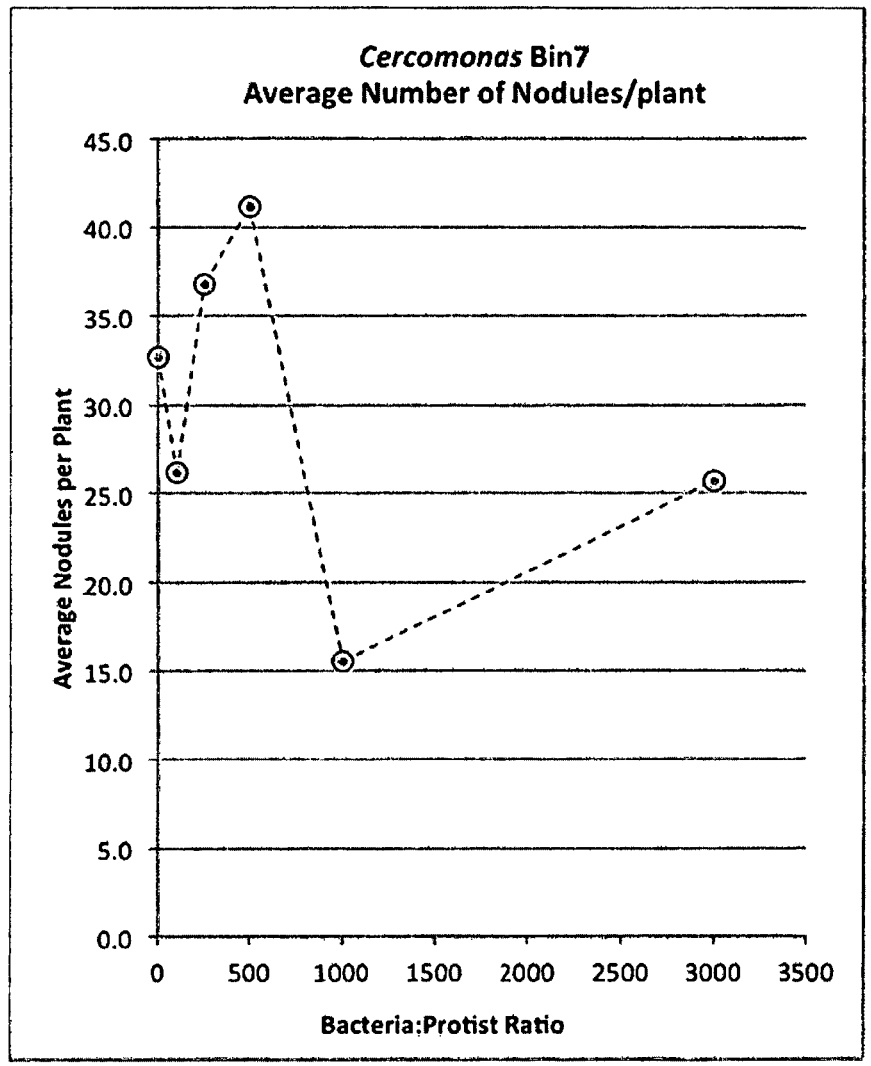
Figure 9C:
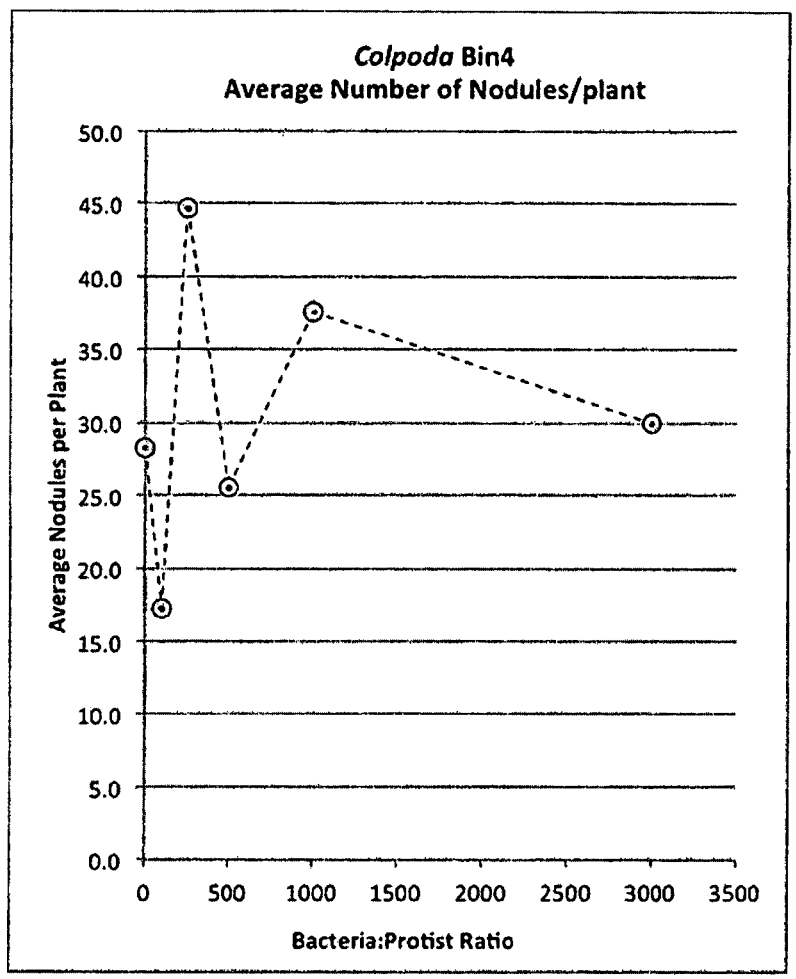

The bacteria and protist quantity test from example 2 was run again, with some modifications. Plants were grown in a mixture of sand and vermiculite to ensure that no residual nitrogen was present in the growth medium. Experimental design was modified to make the quantity and ratio effects easier to dissect. A hole in the pot was filled with two small layers of dry sand: one inoculated with a suspension of protists (bottom layer) and one with bacteria (top layer); this arrangement simulates a granular carrier of the present invention. Pre-germinated bean seeds were placed on top of the bacterial layer and covered. Beans were harvested 3 weeks and 5 days after planting and evaluated as discussed above. Plants displayed abundant nodules, indicating that the sand/vermiculite mix did a satisfactory job of limiting nitrogen. There was a positive, linear correlation (FIG. 9A) between total nodule count and aboveground biomass, which further supports the conclusion that the growth medium was nitrogen limited and that nodules were providing nitrogen necessary for plant growth. When total nodules was plotted against the ratio of bacteria to protists, there was a trend across protist types to display a peak around 100-500 bacteria per protist, with decreased nodulation at ratios above and below that range (FIG. 9B-C).

Materials and Methods for Example 3
1. The soil for this experiment was a sand and vermiculite mixture (1:2:1 course vermiculite:sand:fine vermiculite) that was still nitrogen deficient, but was able to be removed from the rhizosphere a little more easily than the previous mixture. The soil was autoclaved in batches for sterilization.
2. 111 sterile 3"×3"×8" pots were used for this experiment. They were filled with the sterile soil about a week before planting and watered until saturation with $dH_2O$ after filling. They were also watered until saturation with $dH_2O$ the night before the planting.
3. Approximately 300 Zorro™ Black Bean seeds were sterilized as follows:
    a. Shaking in 2% bleach for two minutes;
    b. Thoroughly washed in sterile water;
    c. Shaking in sterile water for two minutes; and
    d. Thoroughly washed in sterile water until bleach smell gone.

The beans were left in sterile water to imbibe for five hours. After imbibing, the seeds were transferred to petri dishes and covered on both sides with wetted, sterile filter paper, where they remained for 24 hours.
4. *R. tropici* was grown in TY (no antibiotics) at 30° C., overnight, on the shaker.

Day of planting:
5. The bacteria were washed twice with 1× Pages (Centrifuged at 14,000 rpm for 2 minutes, resuspended in 1× Pages). The density was taken on the plate reader at $OD_{595}$. The concentration of *rhizobium* used was $1.3*10^9$ cfu/mL/OD. The bacteria was then diluted in 1× Pages to the following concentrations (concentrations per mL found in Table 2 below):
   25,000 cells/150 uL
   250,000 cells/150 uL
   500,000 cells/150 uL
6. Protists counts were taken for both Bin 7 and *Colpoda*. The flasks were observed at 4× to determine basic layout of cysts. Three random spots on each flask were sampled at both 10× and 20×, then the number of cysts were averaged. The field of view dimensions for both magnifications are:
   10×: 1.645 mm×1.095 mm
   20×: 0.84 mm×0.56 mm.
   The flask dimensions used were:
   Narrower: 140 mm×105 mm
   Thicker: 140 mm×115 mm.

(flask dimensions)*(field of view dimensions)=# field boxes which fit in one flask (# field boxes)*(average # cysts per field box)= total # cysts in flask.

The cysts from each flask of its kind were added to determine the total number of cysts. Protists were allowed to grow until reaching numbers greater than what was needed for the experiment (protists are always lost in transfer). At the day of the planting the protist numbers were at 6 million *Colpoda* and 12 million Bin 7.
7. The top layer of liquid from each protist flask was decanted, leaving 5-10 mL behind. The cysts were scraped down from the bottom of each flask into the liquid. The liquids were then combined from their like flasks and centrifuged at 3000 rpm for 5 minutes, checked under the microscope to make sure still living, then centrifuged at 3000 rpm for another 10 minutes.
8. The bacteria and protist treatments were made up in 15 mL falcon tubes and 1.5 mL Eppendorf tubes, respectively. The concentrations and volumes were followed from Table 5 below:

TABLE 5

| Bacteria and protist concentrations per treatment type ||||||||| |
| # Bacteria | Bac:Prot Ratio | # Protists | # per Plug | Conc. per mL | Volume Needed (Min) | Bacteria per 150 uL | Conc. per mL | Volume needed (min.) |
| --- | --- | --- | --- | --- | --- | --- | --- | --- |
| 25000 | 100 | 250 | 14062.5 | 93750 | 450 | 25000 | 166666.6667 | 2700 |
|  | 250 | 100 | 5625 | 37500 | 450 |  |  |  |
|  | 500 | 50 | 2812.5 | 18750 | 450 |  |  |  |

TABLE 5-continued

Bacteria and protist concentrations per treatment type

| # Bacteria | Bac:Prot Ratio | # Protists | # per Plug | Conc. per mL | Volume Needed (Min) | Bacteria per 150 uL | Conc. per mL | Volume needed (min.) |
|---|---|---|---|---|---|---|---|---|
| | 1000 | 25 | 1406.25 | 9375 | 450 | | | |
| | 3000 | 8 | 468.75 | 3125 | 450 | | | |
| | No Protists | 0 | 0 | 0 | 450 | | | |
| 250000 | 100 | 2500 | 140625 | 937500 | 450 | 250000 | 1666666.667 | 2700 |
| | 250 | 1000 | 56250 | 375000 | 450 | | | |
| | 500 | 500 | 28125 | 187500 | 450 | | | |
| | 1000 | 250 | 14062.5 | 93750 | 450 | | | |
| | 3000 | 83 | 4687.5 | 31250 | 450 | | | |
| | No Protists | 0 | 0 | 0 | 450 | | | |
| 500000 | 100 | 5000 | 281250 | 1875000 | 450 | 500000 | 3333333.333 | 2700 |
| | 250 | 2000 | 112500 | 750000 | 450 | | | |
| | 500 | 1000 | 56250 | 375000 | 450 | | | |
| | 1000 | 500 | 28125 | 187500 | 450 | | | |
| | 3000 | 167 | 9375 | 62500 | 450 | | | |
| | No Protists | 0 | 0 | 0 | 450 | | | |

Protists=# protists to develop that ratio;
per plug=# protists per plug for root to intercept an appropriate number or protists;
  Pipet (used to make the holes in the pots) diameter=15 mm and bean root diameter=2 mm, then take the ratio of the areas and find the root occupies 1.77% of hole. 1/0.0117=56.25 (total number of "interceptions" that could fit in the hole).
  56.25*protist #=total # protists per hole.
Concentration/mL=number of protists in 1 mL of 1× Pages (#per plug*(1000/150))
Volume (min)=minimum volume to make for that treatment type.
Bacteria per 150 uL=# bacteria in the treatment type.
Concentration/mL=((bacterial per 150 uL)*(1000/150)).
Volume (min)=minimum volume of bacteria for that treatment type.

9. A 25 mL pipet that had been cut and taped to create a blunt end was used to make two holes at the center of each pot. The holes were made ~3 mL deep and were filled in the following manner, to simulate a granular composition of the invention
1 mL of dry, sterile sand/vermiculite mixture;
150 uL of protist treatment;
1 mL of dry, sterile sand/vermiculite mixture;
150 uL of bacteria treatment; and
1 bean seed with what will be the outgrowth of root facing downward. The sand that had been pushed out from the hole was used to cover up the seed.
Weeks following the planting:
10. Sterile funnels with sterile filter paper cones were placed into the top right corner of each pot and moved to the opposite corner every time the pots were watered. The funnels were filled with dH$_2$O every week day, except for days when the plants received 20 mL of Modified Hoagland's fertilizer.
11. The pots were randomized one week after planting. They were randomly assigned new number (between 1 and 111), then rearranged. This allows for a blind data collection when the plants are pulled from their pots.
12. Once the plants started to grow to a significant size, pots which had two plants were thinned to one. Selection was for the taller, healthier looking plant.
13. Bean plants were harvested after three weeks and five days of growth. This includes:
   a. Clipping shoot growth just above cotyledons and saving in labeled coin envelope for weighing.
   b. Recording coloring and damages to bean leaves.
   c. Gently removing the remainder of the plant out of the pot.
   d. Massaging away soil from root, leaving rhizosphere completely intact, and separating plants in same pot when necessary.
   e. Transferring roots to overhead wash station where rhizosphere is washed away to show nodules.
   f. Laying roots on measuring board where roots are binned every five centimeters. Nodule counts are recorded for each bin.
   g. Drying shoots in the coin envelops in an oven at 85° C. for three days, then cooling in a desiccator until hygrometer reads >10%.
   h. Recording shoot weights.

EXPERIMENT 4

Figure 10A:
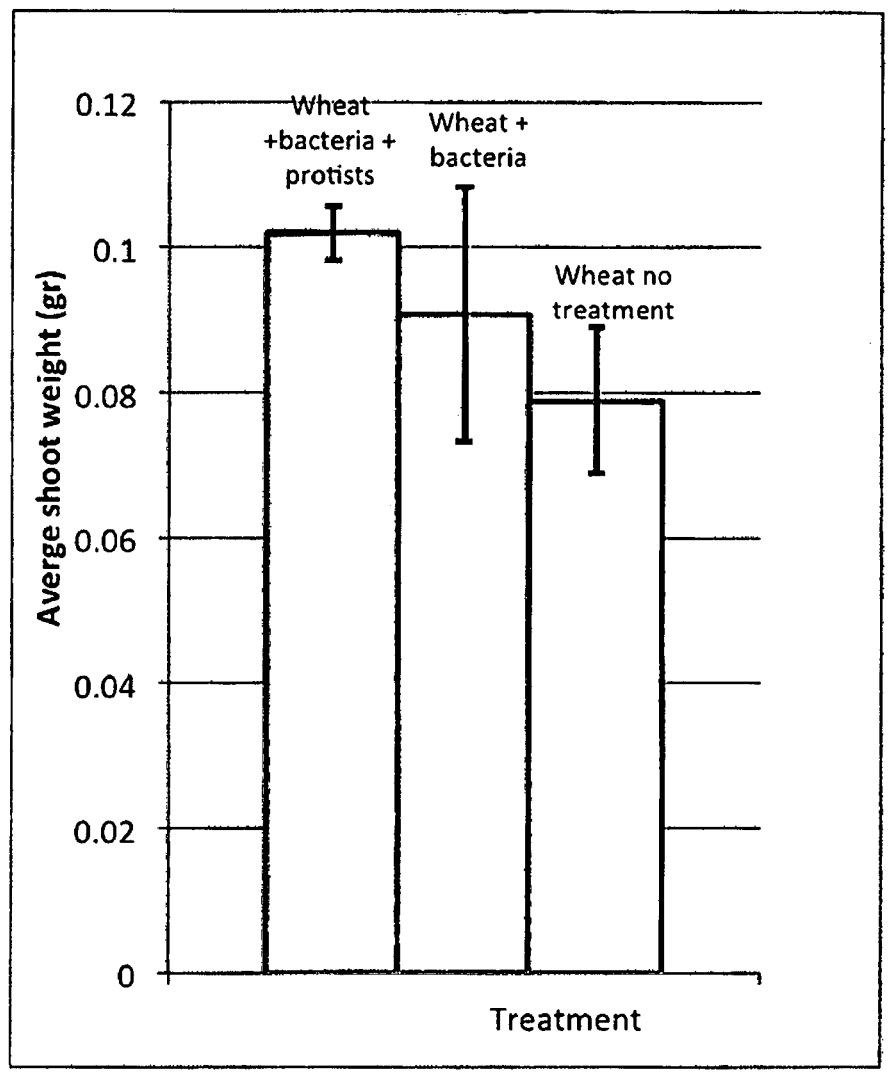
FIG. 10A-B. Wheat shoot weight as a result of treatment with *P. fluorescens* Pf5 with or without added protists. A no-treatment control is also included. The right panel shows results that exclude an outlier shoot in the wheat plus bacteria only treatment (a 0.14 gram shoot). n=4 for the treatments.
Figure 10B:
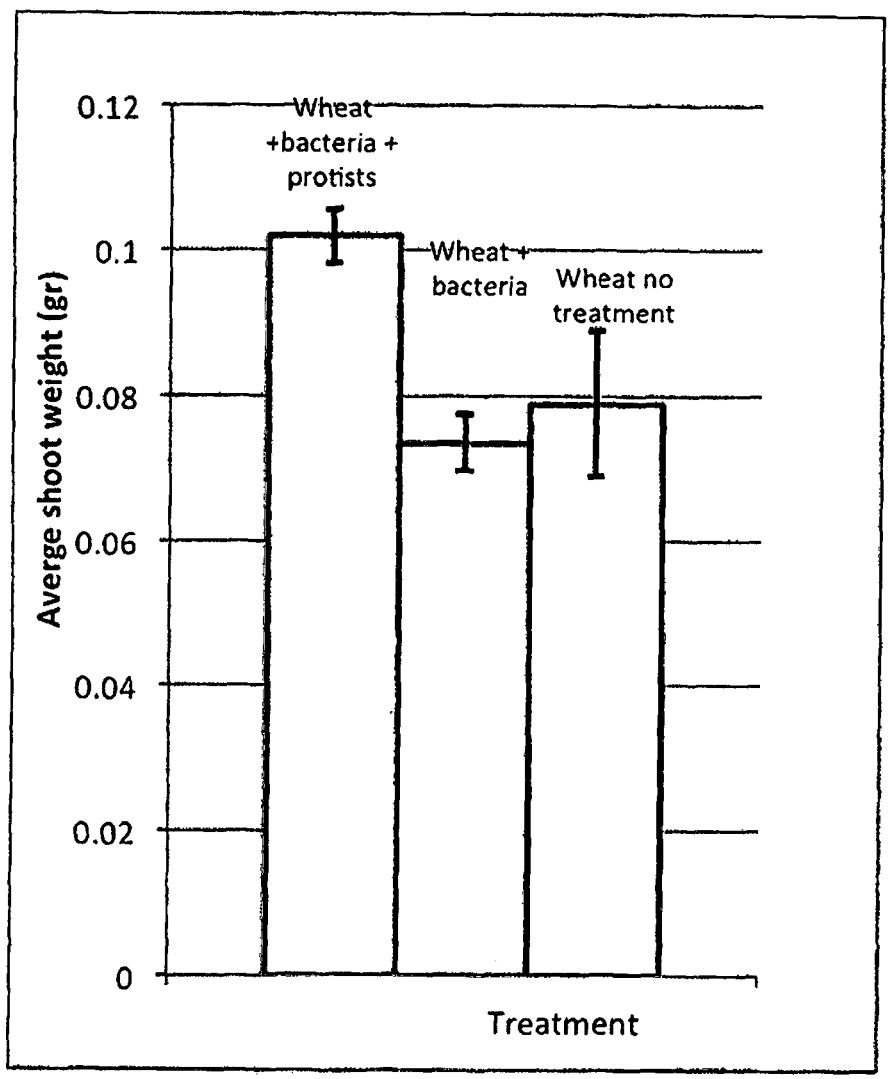

The previous example was conducted with legumes, using nodules as an indicator of effective bacterial colonization along the root system. We next studied wheat, using *Pseudomonas fluorescens* as the symbiont. *Triticum aestivum* cv. Apogee was used for these experiments. This cultivar was bred for dwarf stature and short life cycle, making it conducive to being grown in limited space such as a growth chamber. Examining growth patterns of *P. fluorescens* on wheat roots is more challenging than *R. tropici* on bean roots, where nodulation serves as a clear indicator of bacterial colonization. Landa et al. (2002) outlined a method for quantifying *P. fluorescens* on a given root section using serial dilutions in a 96-well plate with PCR for genotype confirmation. We used this approach, in which 4 replicates of wheat were planted and treated with (a) rifampicin-resistant *P. fluorescens* (Pf5) only; (b) rifampicin-resistant *P. fluorescens* (Pf5) combined with *Cercomonas* sp. (Bin7) protists; and (c) an untreated control. Plants were grown for ~2 weeks before harvest. Roots were broken into three sections, and 1 g samples from each section were agitated in water before being diluted 1:100 into a 96-well plate, where the samples were further serially diluted. Samples from the serial dilutions were transferred into two types of plates filled with different cocktails of antibiotics in order to determine the quantities of rifampicin-resistant Pf5 and total bacteria in the rhizosphere. The results (FIG. 10A-B) indicate that wheat growth is enhanced by a composition comprising bacteria plus Bin7 *Cercomonas* protists compared to the bacteria alone Materials and Methods for Example 4

Prior to Day of Planting

1. The Pf5 strain found in JLM9 was used for this experiment. It is resistant to rifampicin ($Rif_{100}$), which will be a selection system when pulling the bacteria off of the wheat roots. The *pseudomonas* was grown in TY+Km overnight at 30° C. on the shaker.
2. Sixteen 3"×3"×8" pots were filled with greenhouse soil (Fafard#2) and watered until saturation. They were left to drain in the greenhouse for a week prior to planting.
3. Bin 4 and Bin 7 protists were grown in the large culture flasks in 50 mL 1× Pages for approximately ten days. They were fed DH5α at a concentration of $OD_{595}=0.01$.
4. A batch of the 1:2:1 fine vermiculite:sand:course vermiculite mixture was autoclaved and left to cool overnight.
5. The wheat seeds were sterilized using the long sterilization protocol from JG13. There were placed in water in a petri dish and allowed to germinate overnight the day before the planting.

Day of Planting:

6. Protists flasks were decanted and the protists were scraped off the bottom of the flasks using the hard cell scrapers into the remaining liquid. The liquid was then transferred to 15 mL falcon tubes and counts were taken on the microscope. Three spots were used and the numbers were averaged. The counts for Bin 4 were not high enough so the Bin 4 treatment had to be dropped from this experiment. The Bin 7 protists were not concentrated enough. They were separated into 1.5 mL Eppendorf™ tubes and centrifuged at 3,000 rpm for 5 minutes. The supernatant was decanted and the separate tubes were recombined. The protists were then diluted 1:100 in water and the counts were then taken again. It was determined that there were enough protists to have 75,000 protists per plug, and therefore 750 protists would be intercepted by the wheat root.
7. The bacteria that was grown up the night before was washed twice using 1× Pages. The plate reader was used to take the $OD_{595}$ of the bacteria. It was then diluted in 1× Pages so that there were 500,000 bacteria cells per 150 uL.
8. A 10 mL serological pipet was cut and taped to form a blunt edge. One hole was made at the center of thirteen pots about 2 mL deep on the pipet. The holes were filled in the following manner to simulate a granular carrier of the invention:
   i. 1 mL scoop of sand mixture;
   ii. 150 uL protists or 1× Pages (depending on treatment);
   iii. 1 mL scoop of sand mixture;
   iv. 150 uL bacteria or 1 Pages (depending on treatment); and
   v. Wheat seed (emerging root facing downward).

| Pot # | ii | iv |
|---|---|---|
| 1 | Bin 7 | Pf5 |
| 2 | Bin 7 | Pf5 |
| 3 | Bin 7 | Pf5 |

-continued

| Pot # | ii | iv |
|---|---|---|
| 4 | 1X Pages | Pf5 |
| 5 | 1X Pages | Pf5 |
| 6 | 1X Pages | Pf5 |
| 7 | 1X Pages | Pf5 |
| 9 | 1X Pages | 1X Pages |
| 10 | 1X Pages | 1X Pages |
| 11 | 1X Pages | 1X Pages |
| 12 | 1X Pages | 1X Pages |
| 13 | 1X Pages | 1X Pages |

*Pseudomonas* Extraction from Roots:

1. Plants were removed from their pots over a large autoclave bin. The dirt was massaged away, leaving the root system entirely intact.
2. The plants were aligned against a ruler, the crown of the root system aligned with 0 cm, and the length of the longest root was recorded.
3. The shoots were cut at the soil level and placed in coin envelopes. They were dried at 80° C. for three days and then weighed.
4. The root and rhizosphere were collectively divided into three sections: the top 10 cm, the middle 10 cm, and the remaining length. Each section was placed into its own, labeled, plastic sandwich bag.
5. The bags were shaken up and the roots and rhizosphere were massaged.
6. 1.0 g of root/rhizosphere soil samples was placed into a 50 mL conical tube with 10 mL of sterile water. (1:10 dilution)
7. The conical tubes were vortexed in groups of three (the three tubes for each plant were done together) at maximum speed for 1 minute, then sonicated for 1 minute at top power.
8. 2 uL of the slurry was moved into 198 uL of 1× Pages in a 96 well microtiter plate (1:100 dilution).
9. Serial dilutions were done going down the plates, A-H, moving 20 uL from the previous well into a new well with 180 uL 1× Pages (1:10 dilution each time).
10. 50 uL of each well from the 1× Pages plate was transferred to a new 96 well microtiter plate's corresponding well containing 150 uL of $1/10^{th}$ LB-cyclohexamide.
11. 50 uL of each well from the 1× Pages plate was transferred to a new 96 well microtiter plate's corresponding well containing 150 uL of $1/3^{rd}$ $KMB^{+++}rif_{50}$. $1/3^{rd}$ $KMB^{+++}=$
    6.7 g proteose peptone;
    0.4 g $KH_2PO_{47}$
    0.5 g $MgSO_4$-$7H_2O$;
    3.3 mL glycerol;
    15 g/L agar;
    40 ug/mL ampicillin;
    13 ug/mL chloramphenicol;
    100 ug/mL cyclohexamide; and
    pH 7 with HCl or KOH.
12. The 1× Pages plates were kept in the cold room (4° C.) until the end of the experiment.
13. The $1/3^{rd}$ $KMB^{+++}rif_{50}$ and $1/10^{th}$ LB-cyclohexamide microtiter plates were kept in the warm room (30° C.) for 3 days. On day 3 the plates were read on the plate reader at $OD_{595}$. Any well with a reading of $OD_{595}>0.05$ was counted as a positive growth. The terminal most wells of each plant section with positive growth on the $1/3^{rd}$ $KMB^{+++}rif_{50}$ microtiter plates were streaked onto four plates: $\frac{1}{3}^{rd}$ KMB, $\frac{1}{3}^{rd}$ KMB$^{+++}$, $\frac{1}{3}^{rd}$ KMB$^{+++}$rif$_{50}$, $\frac{1}{3}^{rd}$ KMB$^{+++}$rif$_{50}$Km$_{25}$. The corresponding wells on the $\frac{1}{10}^{th}$ LB-cyclohexamide plates were streaked onto their own four plates. The plates were kept in the warm room (30° C.). The $\frac{1}{3}^{rd}$ KMB$^{+++}$rif$_{50}$ and $\frac{1}{10}^{th}$ LB-cyclohexamide microtiter plates were returned to the warm room (30° C.) for another three days to allow for slower growing bacteria.

14. The $\frac{1}{3}^{rd}$ KMB, $\frac{1}{3}^{rd}$ KMB$^{+++}$, $\frac{1}{3}^{rd}$ KMB$^{+++}$rif$_{50}$, and $\frac{1}{3}^{rd}$ KMB$^{+++}$rif$_{50}$Km$_{25}$ plates were allowed to grow for four days. On the fourth day the different types of bacteria growing on the plates were recorded and each bacteria type was transferred from the plate to 100 uL sterile water in a PCR tube.

15. The terminal most consecutive wells with positive growth in the 96 well microtiter plates were used for a PCR identification to determine if the growth was from the Pf5 we inoculated with. The PCR reactions included:
10 uL GoTaq™;
2 uL 10× primer stock (B2BF & BPR4);
7 uL sterile water; and
1 uL template.
The thermocycler was run on PSEU:
95° C. for 3 minutes;
35 cycles of:
 94° C. for 1 minute;
 60° C. for 1 minute; and
 72° C. for 1 minute;
72° C. for 5 minutes; and
10° C. soak.

16. The reactions were run on a 0.8% agarose gel at 100V for 40 minutes.

17. *P. fluorescens* were quantified from wheat root washes using standard techniques.

We claim:

1. A composition, comprising:
(a) an agriculturally suitable carrier;
(b) encysted or sporulated protozoa present in a formulation that is coated over the agriculturally suitable carrier; and
(c) an agricultural payload comprising agriculturally beneficial bacteria; wherein the agriculturally beneficial bacteria are dispersed within the formulation; wherein presence of the protozoa in the composition renders the composition capable of improving plant growth when the composition is administered to soil with an existing plant, or to soil where a plant or seed is to be planted.

2. The composition of claim 1, wherein the agriculturally suitable carrier is selected from the group consisting of seeds, seed coats, granular carriers, liquid slurry carriers, and liquid suspension carriers.

3. The composition of claim 1, wherein the agriculturally suitable carrier comprises a seed or seed coat.

4. The composition of claim 1, wherein the agriculturally suitable carrier comprises a granular carrier, liquid slurry carrier, or liquid suspension carrier.

5. The composition of claim 1, wherein the formulation comprises a biopolymer gel.

6. The composition of claim 1, wherein the formulation comprises a polymer and/or a bulking agent.

7. The composition of claim 1, wherein a protozoa: bacteria ratio in the composition is between about 1:50 to about 1:10,000.

8. The composition of claim 1, further comprising an outer shell enveloping the composition.

9. The composition of claim 1, wherein the protozoa are selected from the group consisting of *Acanthamoeba, Dictyostelium, Heteromita, Vahlkampfia, Stachyamoeba, Proleptomonas,* Class COLPODEA, *Thecamonas, Bodo, Neobodo, Dimastigella, Rhynchomonas, Ochromonas, Spumella, Tetrahymena, Euplotes, Blepharisma, Vorticella, Hartmannella, Phalansterium, Colpoda, Cercomonas, Phalansterium,* and combinations thereof, and combinations thereof.

10. The composition of claim 1, wherein the protozoa comprise protozoa selected from the group consisting of *Colpoda* sp., *Cercomonas* sp., and combinations thereof.

11. The composition of claim 1, wherein the agriculturally beneficial bacteria comprise bacteria selected from the group consisting of Rhizobiales, Psedomonadaceae, Bacillaceae, Rhososprillaceae, Psecomonadaceaea, *Sinorhizobium* species, *Rhizobium* species, *Mesorhizobium* species, *Bradyrhizobium* species, *Bacillus* species, *Pseudomonas fluorescens, Pseudomonas putida, Azospirillum brasilense, Azotobacter vinelandii, Aeromonas veronii, Agrobacterium sp., Alcaligenes piechaudii, Comamonas acidovorans, Enterobacter cloacae, Rhizobium leguminosarum, Paenibacillus polymyxa, Methylobacterium fujisawaense, B. campestris Bacillus circulans DUC1, B. firmus DUC2, B. globisporus DUC3, Alcaligenes sp. Bacillus pumilus, Pseudomonas sp., Variovorax paradoxus , Enterobacter cloacae, Pseudomonas cepacia, L. Enterobacter sakazakii 8MR5, Pseudomonas sp. 4MKS8, Klebsiella oxytoca 10MKR7, L. Pseudomonas sp., Bacillus subtilis, Crocus sativus L, B. cereus, Salvia miltiorrhiza, Azospirillum sp. , Azoarcus sp., Azotobacter sp., Bacillus polymyxa, Burkholderia sp., Gluconacetobacter sp., Herbaspirillum sp., Bacillus amyloliquefaciens, Bacillus pumilus SE 34, Streptomyces marcescens 90-116, Bacillus licheniformis, Paenibacillus polymyxa E681, Enterobacter sp., Pseudomonas aeruginosa, Bacillus amyloliquefaciens, Sinorhizobium meliloti,* and combinations thereof.

12. The composition of claim 1, wherein the agriculturally beneficial bacteria comprise *Pseudomonas fluorescens* or *Sinorhizobium meliloti*.

13. A method for improved plant growth, comprising delivering the composition of claim 1 to soil with an existing plant, or to soil where a plant or seed is to be planted.

* * * * *